United States Patent
Mailling et al.

(10) Patent No.: US 8,320,648 B2
(45) Date of Patent: Nov. 27, 2012

(54) METHOD OF PREPARING A MEDICAL RESTRAINT

(75) Inventors: Michael Mailling, Cornwall (GB); John Wright, Cornwall (GB)

(73) Assignee: Axellis Ventures Ltd, Leicestershire (GB)

( * ) Notice: Subject to any disclaimer, the term of this patent is extended or adjusted under 35 U.S.C. 154(b) by 939 days.

(21) Appl. No.: 12/162,573

(22) PCT Filed: Jan. 30, 2007

(86) PCT No.: PCT/GB2007/000303
§ 371 (c)(1),
(2), (4) Date: Dec. 10, 2008

(87) PCT Pub. No.: WO2007/085864
PCT Pub. Date: Aug. 2, 2007

(65) Prior Publication Data
US 2009/0316965 A1 Dec. 24, 2009

(30) Foreign Application Priority Data
Jan. 30, 2006 (GB) .................................. 0601801.4

(51) Int. Cl.
*G06K 9/00* (2006.01)
(52) U.S. Cl. ........................................ 382/128; 382/285
(58) Field of Classification Search .................. 382/124, 382/128, 285
See application file for complete search history.

(56) References Cited

U.S. PATENT DOCUMENTS

| | | | |
|---|---|---|---|
| 5,432,704 A | 7/1995 | Vouzelaud et al. | |
| 5,596,504 A | 1/1997 | Tata et al. | |
| 5,683,243 A | 11/1997 | Andreiko et al. | |
| 6,564,086 B2 * | 5/2003 | Marchitto et al. | 600/425 |
| 6,748,400 B2 | 6/2004 | Quick | |
| 2001/0044668 A1 | 11/2001 | Kimbrough et al. | |
| 2004/0186744 A1 | 9/2004 | Lux | |
| 2006/0015202 A1 | 1/2006 | Sweat | |
| 2007/0033786 A1 | 2/2007 | Bradley | |
| 2007/0226986 A1 | 10/2007 | Park et al. | |
| 2008/0027974 A1 | 1/2008 | Collins | |

FOREIGN PATENT DOCUMENTS

DE 3340482 5/1985
(Continued)

OTHER PUBLICATIONS

International Search Report for PCT/GB2007/000303, mailed Jul. 29, 2008.
(Continued)

*Primary Examiner* — Phat X Cao
(74) *Attorney, Agent, or Firm* — Brown Rudnick LLP

(57) ABSTRACT

A method for preparing a clinical restraint for a subject, the method comprises scanning the portion of the subject to be restrained to produce a 3D image data set, generating a three dimensional replica of the portion of the subject from the 3D image data set and preparing a clinical restraint using the three dimensional replica. A scanning system for generating the 3D image data set comprising one or more projectors (6) and one or more cameras (8) in combination with an image processing device is also disclosed. The imaging aspects are also applied in the monitoring of the treatment of a patient, the manufacture and fitting of medical items, such as compression hosiery and the like, as well as in the fitting of garments and items of clothing.

23 Claims, 14 Drawing Sheets

FOREIGN PATENT DOCUMENTS

| | | |
|---|---|---|
| DE | 4102258 | 7/1992 |
| EP | 2108401 A1 | 10/2009 |
| WO | 99/58929 | 11/1999 |
| WO | 0045283 A1 | 8/2000 |
| WO | 01/82829 | 11/2001 |
| WO | 2010019504 A1 | 2/2010 |
| WO | 2011024085 A1 | 3/2011 |

OTHER PUBLICATIONS

Anders Ahnesjö et al: "Review; The IMRT information process-mastering the degrees of freedom in external beam therapy", Physics in Medicine and Biology, Taylor and Francis Ltd. London, GB, vol. 51, No. 13, Jul. 7, 2006, pp. R381-R402.

International Search Report and Written Opinion mailed Jun. 12, 2012 for PCT/US2012/030706 (11 pages).

Galvin et al: "Alternative Methods for Intensity-Modulated Radiation Therapy Inverse Planning and Dose Delivery," Seminars in Radiation Oncology, Saunders, Philadelphia, PA, vol. 16, No. 4, Oct. 1, 2006, pp. 218-223.

Chang S X et al: "Compensators: An alternative IMRT delivery technique," Journal of Applied Clinical Medical Physics, American College of Medical Physics, Melville, NY, vol. 5, No. 3, Jan. 1, 2004, pp. 15-36.

International Search Report and Written Opinion mailed Jun. 18, 2012 for PCT/IB2012/000793 (11 pages).

* cited by examiner

METHOD OF PREPARING A MEDICAL RESTRAINT

CROSS REFERENCE TO RELATED APPLICATION

The present application claims priority from PCT patent application Ser. No. PCT/GB2007/000303 filed 30 Jan. 2007 and GB Patent Application GB0601801.4 filed 30 Jan. 2006.

The present invention relates to a method of preparing a medical restraint, in particular, but not limited to, a clinical restraint for the head of a patient undergoing radiotherapy. In further aspects, the present invention relates to a method for imaging a patient and to procedures employing such imaging.

Many surgical procedures require the relevant parts of the patient to be immobilized. One procedure in which the immobilization of the patient is essential is radiotherapy. The treatment of any tumor in the head or neck of a patient requires the patient's head to be restrained and prevented from moving. The restraint employed for such treatments is an immobilization mask. The mask, moulded to the contours of the face of the patient, fits over a large portion, in many cases substantially all, of the head of the patient and is anchored to the operating table. In some cases, the restraint is required to extend over the head and shoulders or upper torso of the patient. The mask operates to keep the head of the patient still during the radiotherapy treatment.

By restraining the head of the patient in this manner, the clinician can be sure that the target site can be accurately irradiated. This ensures that the tumor is efficiently treated. In addition, this minimizes the exposure of tissue outside of the target area to potentially harmful radiation. In a prolonged treatment of a patient, it is important that the portions of the patient undergoing irradiation are immobilized in a consistent manner. This frequently extends over a series of treatment sessions. The mask or restraint must therefore act to restrain the patient in a consistent way over an extended period of time. To assist the surgeon in maintaining the accuracy of the irradiation over repeated treatments, reference marks may be transposed onto the mask, rather than the anatomy of the patient.

The mask must be prepared from a material that is sufficiently transparent to the radiation being employed and to allow the clinician to view the patient underneath. If properly formed, the mask can assist in directing and focusing the radiation beam to the target area.

A number of different techniques may be used to prepare a medical restraint. In one method, to prepare a restraint, a plaster cast is made of the limb or area of the patient to be treated. As a first step in this procedure, a liquid, thermosetting polymer is poured over and applied to the limb or area. Thereafter, strips of cloth or bandages impregnated with plaster of paris are applied to provide additional support to the thermosetting polymer both while it sets and thereafter. Once the polymer and the plaster have both fully set, the cast is lifted from the patient. The cast is then used to prepare a replica of the limb or portion of the patient, which is thereafter used to form the final mask in a polymer by vacuum forming techniques. A transparent polymer is often preferred, in order to allow the clinician to see the skin of the patient beneath the restraint. The final mask is then fitted to the patient and adjusted accordingly, in order to ensure that the mask will act as a suitable restraint, before the radiotherapy procedures can be carried out.

As will be appreciated, the process of preparing the cast of the patient is a time consuming and labour intensive task. During this time, the patient must remain motionless. Movement by the patient during the casting procedure will reduce the accuracy of the final mask and, if the movement is excessive, the entire procedure must be repeated. The problems of keeping the patient motionless during the cast forming procedures are more acute when the patient is a child, whose natural tendency is to move during such a procedure. This procedure has also been identified as being the most traumatic part of the entire treatment regime for many patients and, as a rule, patients do not like the procedure for preparing a restraint or mask by the casting process.

In general, even if the patient is kept motionless, the cast and the final mask are often inaccurate and are not possible to fit properly to the patient. This is caused, in part, by the need for contours of the patient's limb to be sculpted by hand, as a result of poor reproduction using the casting process. In addition, lifting the cast from the patient often results in damage or distortion of the cast, which is in turn reflected in the final mask. Further, the body of the patient can change shape during the procedure, resulting in the final mask being a poor fit.

An alternative procedure to casting relies on the use of a thermoplastic polymer to prepare the mask directly by moulding onto the patient. An example of a commercially available product of this kind is EFFICAST®, available from Orfit Industries. The thermoplastic polymer product is provided in the form of a perforated sheet of polycaprolactone coated with a dispersion of an acrylate-urethane. In use, the sheet is softened by heating to a temperature of about 65° C., for example in a water bath. The softened sheet is then applied to the portion of the patient to be restrained, for example the face, and moulded by hand to follow the contours of the patient. Once cooled, the sheet becomes rigid and retains the shape of the patient.

This method suffers a number of disadvantages. First, it is important to heat the sheet to a specific temperature for a specific length of time, both of which must be carefully monitored. Failure to follow this procedure properly will result in the sheet being too soft or, in the alternative, to rigid, to mould properly to the patient. Second, as the sheet begins to cool as soon as it is removed from the water bath or other heating means, the clinician only has a very limited amount of time in which to complete the moulding procedure. Failure to complete the moulding procedure in this time will result in the sheet material becoming too hard to work. Further, holes are required in the mask for the patient's eyes, nose and mouth and these must be cut in the material after it has cooled. As the material is difficult to cut, this cutting procedure is difficult to complete accurately and safely.

A particular problem arises in cases where the portion of the subject's body to be restrained is composed of soft tissue. The known casting procedures set out above do not work well with soft tissue portions of the body, as the action of the casting process and the weight of the casting material will deform the soft tissues, leading to large inaccuracies in any restraint that is prepared from the cast. Accordingly, because of the difficulties of casting soft tissues, procedures such as the irradiation of a breast to treat breast cancer are carried out without any immobilization of the breast itself.

Finally, the treatment of the patient by radiotherapy typically requires repeated exposures to radiation over an extended period of time. During the time of the treatment, any changes in the body of the patient, for example due to weight gain or loss, will render the restraining mask useless, as the accuracy levels of radiological treatment are reduced if the patient is able to move around inside the mask or restraint. Such a situation requires the entire procedure to be repeated and a new mask or restraint to be made.

Accordingly, there is a need for an improved procedure for the preparation of clinical restraints for use in restraining patients during medical procedures, in particular radiation therapy. The need is particularly acute in the preparation of restraining masks for holding the head of a patient still during the treatment of the head and/or neck. In addition, there is a need for a method of preparing accurate clinical restraints for areas of soft tissue that hitherto have not been capable of restraint during irradiation and other procedures.

In a first aspect, the present invention provides a method for preparing a clinical restraint for a subject, the method comprising:

scanning the portion of the subject to be restrained to produce a 3D image data set;

generating a three dimensional replica of the portion of the subject from the 3D image data set; and preparing a restraint using the three dimensional replica.

The method of preparing a clinical restraint may be carried out and completed in the same facility as the initial scanning of the patient to provide the set of 3D image data. However, the patient may be scanned and the 3D image data set prepared in one location and transmitted to a remote location in order to prepare the replica and the restraint. Accordingly, in a second aspect, the present invention provides a method for preparing a clinical restraint for a subject, the method comprising:

providing a 3D image data set obtained from scanning the portion of the subject to be restrained;

generating a three dimensional replica of the portion of the subject from the 3D image data set; and preparing a restraint using the three dimensional replica.

In a further aspect, the present invention provides a method of conducting a medical procedure requiring a portion of the subject to be restrained during the medical procedure, the method comprising:

scanning the portion of the subject to be restrained to produce a 3D image data set;

generating a three dimensional replica of the portion of the subject from the 3D image data set;

preparing a clinical restraint using the three dimensional replica; and restraining the portion of the subject with the restraint.

The method of the present invention provides very accurate immobilization devices or restraints for very close fitting to the portion of the subject to be restrained during the clinical procedure, in particular radiological treatment of a portion of the subject. As the method does not require any physical interaction with the subject, there are none of the problems associated with known procedures. In particular, there is nothing to deform the portion being reproduced, allowing the replica and the final restraint to be very accurate. A particular advantage is that soft tissue portions, such as breasts, may be imaged and restraints prepared.

The method of the present invention employs, as a first stage, the production of a 3D image data set representing the portion of the subject to be restrained. Suitable imaging procedures are known in the art. In one suitable imaging method, the 3D image data set is prepared by a method comprising the steps of:

illuminating the portion of the subject with a light pattern having a plurality of light planes, the light pattern varying in wavelength spatially across the portion of the subject and wherein said at least one light plane corresponds to at least one angle at which light of that wavelength is emitted and contains only a single spectral component;

acquiring an image of the portion of the subject thus illuminated using a camera; and calculating a distance to a point on said object or in said scene using triangulation based on a baseline distance between said light source and the camera, an angle between the camera and the baseline and an angle at which light striking the point is emitted by the light source as determined from red/green/blue values corresponding to the wavelength of the light striking the point.

Preferably, in the illuminating step the light pattern is varied over the visible light spectrum, the infrared light spectrum or the ultraviolet light spectrum. Such an imaging method is described in WO 02/059545, the disclosure of which is incorporated herein by reference.

It is preferred that the portion of the patient to be restrained, for example the head and shoulders or upper torso, is scanned on each occasion to provide a 180 degree image data set. This is particular advantageous when preparing a restraint for a patient's head, as the 180 degree image data set allows a more accurate replica of the complicated contours of the patient's face and head to be prepared.

A particularly preferred method of generating the 3D image data set is one comprising the steps of:

projecting a predetermined pattern of components onto the portion of the subject, the components having a known relative positioning;

acquiring an image of the portion of the subject; and calculating the three-dimensional shape on the basis of relative distances between pattern components as observed in the acquired image.

The predetermined pattern of components is preferably a grid or a series of grid patterns. The pattern is preferably projected using digital light processing (DLP) techniques, known in the art. The 3D image data set may be obtained using a single DLP unit and a single camera. In order to obtain a 180 degree image data set of the target area, two or more cameras are used with a single DLP unit. In preferred embodiments, a plurality of DLP units are used, preferably in conjunction with a plurality of cameras. If a plurality of cameras are used, the result will be a plurality of separate images of the target area. These images are then combined or 'stitched' together, in order to form a single image data set for the target area. Such image stitching techniques and computer software for their implementation are known in the art. An example is the FaceSnatcher product available from Eyetronics N.V.

Preferably, absolute dimensions of the portion of the subject are obtained by fixing an appropriate scale factor. In the method, the relative spatial positions of points on the portion of the subject are preferably calculated directly from relative, observed positions of the components of the image. In a preferred embodiment, the pattern of components comprises a plurality of lines, in particular a grid of straight lines. The grid of straight lines preferably comprises two series of parallel lines, the lines of one series being orthogonal to the lines of the other series.

The pattern of lines and/or the pattern of intersections of the lines are preferably extracted from the acquired image. In a preferred embodiment, each line and/or each intersection is extracted from the acquired image. Most preferably, intersections of the lines are determined and the relative positions thereof in the pattern are associated with relative sequential numbers. The positions of the lines may be refined by a regularisaton technique.

In this preferred method, the imaging system may be calibrated by presenting two planes which subtend a known angle.

Such a method of producing a 3D image data set is disclosed in EP 1 009 969, the disclosure of which is incorporated herein by reference.

In one preferred embodiment, the 3D image data set is processed and modified before being used in the preparation of the replica. In particular, the 3D image data set may be modified to interpolate and fill in omitted data, such as details hidden from the camera during the imaging step. In addition, and preferably, the 3D image data set is processed to remove undercut portions of the image and modify the image to provide the replica formed from the image data set with the appropriate tapered form or draft. This is necessary in order to facilitate the removal of the mask or restraint from the replica once it has been formed. Such techniques of forming the replica are well known in the field of moulding and vacuum forming.

In addition, the 3D image data set may be processed and modified to extend the sides of the image so as to reach the surface on which the portion of the patient or subject will be restrained. For example, when preparing a restraint for the head of a patient, the 3D image data set generated during the imaging step is modified to remove the undercut formed by the neck and chin and extend the sides of the face of the patient to reach the operating table. The processing step may also modify the image data set to include holes for various parts of the subject, as required, for example holes for eyes, nose and mouth in restraints intended for the head of a patient.

In one embodiment, the imaging system provides the clinician with a display with which to view the 3D image data set. This will allow the clinician to see both the raw image data set and an image of the completed restraint. The system may be interactive and allow the clinician to modify the 3D image data set, for example to provide additional holes in the restraint or enlarge existing holes for the eyes, nose or the like.

Further, as the restraint is required to fit and be secured to a particular treatment table or the like, the system may include a provision whereby the clinician may input details regarding the number and nature of the means of attaching the restraint to the treatment surface or other such details. If the system is being used repeatedly at a given location, the details of the treatment table and the securing means may be input into the data processor as standard settings, to be used in the processing of all data images to produce 3D image data sets that conform to the circumstances of the specific location. In such a case, the system is preferably provided with an override facility, allowing the clinician to modify the design of a particular restraint.

Further, as the 3D image data set provides an image related to the exact size and shape of the imaged portion of the subject, the replica and the eventual restraint or mask will be similarly sized. This may result in the restraint being too tight when fitted to the patient. Accordingly, the processing of the raw image data to produce the 3D image data set preferably includes provision for changing the dimensions to ensure a suitable fit to the patient. The change in size may be incorporated into standard image processing routines and applied automatically to the raw image data. Alternatively, the required size modification may be input by the clinician or other operator. If an automatic processing routine is used to modify the size, it is still preferred to provide the clinician with an override facility, whereby the size may be adjusted either globally across the entire image or locally. Local size adjustment may be required where the patient has a sensitive skin condition, for example arising from a tumour close to the surface of the tissue. In addition, radio therapy may induce certain side effects, such as swelling of tissue in and around the treated area. Further, the patient may experience inflammation or swelling of other regions, such as the throat, in which case allowances may be made in the 3D image data set to size the restraint accordingly to accommodate any expected swelling or other physiological change. It is understood that any adjustments in the eventual size of the restraint by modification of the image data should not compromise the ability of the restraint to immobilize the patient.

Further, the 3D image data set may be modified to compensate for changes in dimensions of the eventual restraint that may arise during its preparation, for example to compensate for expected shrinkage of the restraint during the vacuum forming process. Again, such compensation may be applied across the entire image or may be limited to one or more localized areas.

The 3D image data set is preferably compiled to include a coloured image of the portion of the subject, in particular in a format that allows the colour image to be printed onto a two-dimensional, that is flat, or three-dimensional surface.

In many medical procedures, the surface of the portion of the subject being treated and/or the restraint or mask is marked with indications to guide the clinician or other medical practitioners. For example, the skin of the subject may be marked with indications to provide a target for the irradiation. It is an advantage that such indications may be incorporated into the restraint during the method of its preparation, thus obviating the need to mark the patient at the beginning of each procedure. Accordingly, in one embodiment, the replica is provided with indications on its surface for use in guiding the surgical procedure. The indications formed on the replica may be derived from indications placed onto the surface of the portion of the subject and captured in the image during the imaging step. The method may further comprise the step of forming indications on the restraint corresponding to the indications formed on the surface of the replica. In one preferred embodiment, the indications are formed as raised portions of the surface of the replica, such that corresponding impressions are formed on the inner surface of the clinical restraint directly during the step of forming the replica. These techniques obviate the need to mark the restraint or mask after it has been formed, thereby reducing inaccuracies that may arise in transcribing marks from a source, such as a photograph or the like to the restraint or mask.

In an alternative embodiment, the replica is used to prepare a second component for use in the procedure which carries the surgical indications. Thus, the method may further comprise the step of preparing a flexible layer from the replica to lie between the restraint and the outer surface of the portion of the subject. Such a flexible layer, may be a coloured representation of the portion of the subject. This is particularly useful when treating such areas as the face of the patient. The flexible layer may comprise a coloured image of the complete portion of the subject or just a part thereof. Such a coloured image is useful, for example, to allow the surgeon or clinician to identify surface blemishes or features, such as lesions or moles, which are to be avoided during the medical procedure. For example, in the case of treatment by irradiation, it is preferred not to irradiate damaged skin tissue, such as lesions, cuts or bruises. In such a case, the flexible layer may be provided with indications of use in guiding the surgical procedure. The flexible layer may be vacuum formed over the surface of the replica. Alternatively, the flexible layer is formed as an image on a flat sheet, often referred to as a 'texture', from the 3D image data. The flat sheet may then be formed around the surface of the replica by means of a vacuum. A coloured image may be formed on the flat sheet by conventional printing processes known in the art.

In one preferred embodiment, the method allows the clinician, such as the radiographer, to include in the 3D data set all marks and indications required for use during the medical procedure to be conducted. These may be transposed onto the restraint or mask as noted hereinbefore. In addition, the method may be operated to allow the clinician or other technical person to input into the 3D data set details to be incorporated into the preparation of the restraint or mask. For example, the clinician may wish to mark out the areas of the raw restraint to be removed to accommodate the eyes, ears, nose and mouth of the patient. Such marks may be incorporated into the replica, as noted hereinbefore and/or into the flexible layer. It is particularly preferred that the marks are incorporated into the surface of the replica and transposed directly onto the inner surface of the mask or restraint. In such a case, the marks may be easily followed by the technician finishing the restraint (as described hereinafter), who can be sure that the wishes of the clinician are being met. The finishing of the restraint may be completed at the site of production of the raw restraint or elsewhere, following the marks. Accordingly, a raw or partially finished mask or restraint may be supplied to the hospital or clinic, for final finishing by the clinician, or more likely, a technician assistant.

Suitable techniques for preparing the replica from the 3D data set are known in the art. Examples of preferred techniques include 3D printing techniques, including colour 3D printing, stereolithography (SLA), vacuum casting, selective laser sintering (SLS), rapid cast metals, direct metal laser sintering (DMLS), laminated object manufacture (LOM), fused deposition modeling, 3D thermojet wax modeler rapid tooling, injection moulding, CNC machining, micro-modeling and blow moulding. In one embodiment, the replica is prepared in the form of an array of longitudinal movable pins, the displacement of each pin from a datum being determined from the 3D image data, such that the surface of the replica is formed from the ends of the plurality of pins. Such pin assemblies are known for forming three-dimensional surfaces.

The replica may be produced either wholly or in part in colour, in particular with an image of the portion of the subject to be restrained, for the reasons set out above with respect to the use of a coloured flexible interlayer.

The restraint or mask is formed on the surface of the replica. This may be accomplished using a range of techniques known in the art. One particularly suitable technique is by vacuum forming, in which a sheet of material is formed in three dimensions over the surface of the replica. Once the raw restraint has been prepared, it is then trimmed and finished. This may be an automatic procedure, may be carried out by hand, or may be a combination of both. The finishing process includes removing excess material from the raw restraint. In addition, the restraint is modified to include such features as openings for a patient's eyes, nose and mouth, in the case of a head restraint. In order to accurately form the openings for eyes, nose and mouth, the use of a replica or flexible underlay having a full colour image of the subject is advantageous. In this way, the precise position and size of the various openings can be readily identified.

The restraint is most preferably transparent, providing the surgeon with a complete view of the portion of the subject beneath. The restraint may be formed so as to enhance the medical procedure. For example, in the case of a irradiation, the restraint may be formed with a lens portion to focus the incident radiation onto the target area, thus minimizing the scatter of irradiating light and the possible damage to surrounding tissue. In some cases, it may be advantageous for the restraint to have substantial portions translucent or opaque, with just the target area being left completely transparent. This may serve to protect the tissue surrounding the target area, depending upon the procedure being carried out.

The method of the present invention is suitable for the preparation of a restraint for any part of the human or animal anatomy. The method is particularly suitable for the production of a head restraint. As noted above, it is a significant advantage of the present invention that restraints for soft tissue portions, such as breasts, may be prepared.

A further aspect of the present invention provides a replica formed by the method as hereinbefore described.

Still a further aspect of the present invention provides a restraint prepared by the method as hereinbefore described.

According to the present invention, there is also provided a method of conducting a surgical procedure on a portion of a subject, the method comprising restraining the portion of the subject using a restraint prepared by a method comprising the steps of:

scanning the portion of the subject to be restrained to produce a 3D image data set;

generating a three dimensional replica of the portion of the subject from the 3D image data set; and preparing a clinical restraint using the three dimensional replica.

The procedure may be any procedure where with restraint and immobilization of one or more portions of the patient is required. For example, the procedure may comprise irradiation of a portion of the subject. The portion of the subject may be the subject's head or a portion thereof or a breast. In some cases, the restraint is required to fit large portions of the subject's body, for example the entire head and neck, or head, neck and shoulders.

In a further aspect, the present invention provides a system for preparing a 3D image data set for the preparation of a clinical restraint, the system comprising:

a projector for projecting an array of components onto the surface of the subject to be restrained;

a camera for capturing an image of the surface to provide raw image data;

a processor for preparing a 3D image data set from the raw image data;

a display means for displaying the 3D image data as an image;

a processor for modifying the 3D image data set according to a set of predetermined functions, thereby rendering the 3D image data set suitable for use in the preparation of the restraint.

The system may comprise a single projector and a single camera. However, preferred systems are those comprising a plurality of projectors and/or a plurality of cameras. The system preferably comprises a plurality of imaging sub-systems, each sub-system comprising a projector and a camera.

A preferred system is one in which the processor is adapted to combine a plurality of raw images to form the 3D image data set. In this way, raw image data from a plurality of cameras may be combined to form the 3D data image set. The processor is preferably adapted to modify the 3D image data set, in particular by one or more of:

interpolating to fill in missing image data;

removing undercut portions of the image data;

providing the image with an appropriate taper or draft for moulding;

extending the image to provide a region of attachment to a treatment platform or the like; or providing one or more holes in the image.

In addition, the system is preferably configured to allow the 3D image data to be processed to increase the size of a portion of the whole of the image to provide a clearance between the subject and the restraint.

The system preferably comprises an interface, whereby an operator may input data for inclusion in the 3D image data set and/or modify the image of the 3D image data set.

As described hereinbefore, the methods of the present invention advantageously use a full colour image of the portion of the subject. Accordingly, the camera is preferably adapted to capture a full colour image of the surface of the subject, the full colour image (known as the texture) becoming a part of the 3D image data set.

The aspects of the present invention relating to the preparation of an image of a portion of a subject have applications beyond the preparation of a clinical restraint or the use thereof, as will be described.

In many conditions of the human or animal body requiring treatment, a problem exists in monitoring the progress of a patient or subject in recovering from the condition ailing them. Very many conditions require repeated visits by the sufferer to a healthcare specialist, such as a doctor, surgeon or physician. During these repeated visits, the healthcare specialist reviews the patient by inspecting the relevant portion or portions of the patient and attempting to make a comparison with condition of the same portion or portion during the previous visits. Notes or measurements may be taken to assist the healthcare specialist. However, this can only at best be a very inaccurate manner of monitoring progress.

A further example of a condition requiring such monitoring and assessment is the treatment of tumours. In many cases, tumours manifest themselves as a change in the shape and/or size of a particular portion of the patient's body. Equally, treatment of the tumour may be monitored if the change in shape or size of the affected portion or area can be assessed. Accordingly, there is a need to provide a method for such a method of monitoring. In many cases photographs and/or measurements are taken during successive visits of the patient to the healthcare specialist. However, it remains difficult to compare such photographs and measurements and it is very difficult to gain a clear understanding of the change in physical shape of the subject and, hence the progress of the treatment.

A further example is the fitting of medical compression stockings to patients. Compression stockings are required to provide an accurate level of compression to counter swelling of the limb. In particular, the stocking must provide a distributed pressure to the limb, with the compression pressure being graduated from one end of the stocking to the other. In this way, the vascular system of the patient is constricted, thereby increasing the velocity of the blood flowing through the blood vessels. As the treatment relies upon the application of the correct amount of pressure, as time progresses, it is necessary to change the compression stocking in response to changes in the size and shape of the limb being treated. In order to ensure the correct fit for the first and subsequent compression stockings, an accurate measurement and monitoring of the dimensions of the limb are required.

Accordingly, in a further aspect, the present invention provides a method of monitoring the physiological changes in a subject, the method comprising:

scanning the portion of the subject to be monitored to produce a first 3D image data set at a first point in time;

scanning the portion of the subject to be monitored to produce a second 3D image data set at a second point in time, different to the first point in time;

comparing the first and second 3D image data sets to identify any differences between the two data sets; and relating the identified differences between the first and second data sets to features of the portion of the subject.

The steps of scanning the portion of the subject may be performed using the techniques as hereinbefore described.

The method of the present invention may be used to monitor any condition or ailment that results in a change in the outward shape or appearance of the subject. Examples include any condition that gives rise to an inflammation or swelling of any portion of the body. Each 3D image data set may also comprise a colour image of the relevant portion of the patient or subject, thus allowing the clinician to compare the appearance of the skin of the region of the patient undergoing treatment. In many cases, progress of the treatment may be monitored by changes in both the dimensions and shape of the relevant region, as well as its outward appearance. The treatment or monitoring of features such as moles, cysts, warts, skin tags or lesions may benefit from the clinician being able to make a direct visual comparison of images taken at various stages in the treatment, together with obtaining a comparison of the physical shape and dimensions of the region being treated. Such a technique may be used in the monitoring of a patient to identify at an early stage the onset of a particular condition, as well as monitoring the progress of the treatment of an existing condition. For example, the imaging method employing both dimensional comparison and visual comparison may be used to detect changes in the shape, size and colour of a mole or other skin imperfection in a programme for the early identification of skin cancers.

For example, there is currently a need for a procedure allowing a radiotherapist to quickly and accurately assess a patient immediately prior to a session of radiotherapy. In particular, the radiotherapist is anxious to ensure that the patient is in a proper condition to undergo the further treatment. The method of the present invention may be applied to provide the radiotherapist with an accurate set of image data to determine the state of the patient. Accordingly, in one embodiment, the method of monitoring of the present invention is used to check and verify a patient immediately prior to a session of radiotherapy. In particular, the patient is scanned and a 3D image data set generated before the radiotherapy begins. The scanning procedure may be one to produce a 180 degree image data set, or the same procedure as used to generate the earlier 3D image data sets and to prepare the most recent clinical restraint. This may be done in the radiotherapy theatre or some other local location. The radiotherapist is thus provided with a 3D image data set of the patient that may be compared directly with a 3D image data set produced earlier in the treatment. This allows any changes in the physiology of the patient to be identified, such as weight gain, weight loss, swelling and the like. This in turn allows the clinician to determine, for example, if the existing restraint is still suitable to restrain and immobilize the patient. If so, the therapy session may continue as planned. If not, the patient may be asked to return, once a new restraint of the appropriate fit has been prepared. In this way, the loss of time for both the patient and the clinician is minimized, as is the level of discomfort to be endured by the patient.

In one particular embodiment, this aspect of the present invention is used in the monitoring of the swelling in a patient's legs. In many patients, particularly the elderly, swelling and inflammation of the legs, especially the lower legs, is a major problem. One cause of such swelling is chronic leg ulcers, affecting principally the elderly. The key risk factors for leg ulcers include increasing age, obesity, immobility, peripheral oedema, varicose veins and deep vein thrombosis (DVT). The known practices for treating such swelling is to provide the patient with an elastic stocking to cover the affected area and maintain a constant pressure on the limb, to improve the blood flow. Indeed, chronic leg ulcers respond well to compression therapy, provided that clinically effective levels of compression are applied to affected area and maintained for an extended period time. One of the most significant applications for compression hosiery is in the primary prevention of long term vascular complications.

Compression hosiery includes socks, stockings and tights and is worn for a number of reasons, including prevention of venous leg ulcer recurrence following the initial healing of the wound, healing of venous leg ulcers, primary prevention of leg ulcers as a result of varicosed veins, prevention of deep vein thrombosis (DVT), prevention of complications following the treatment of DVT and the maintenance of reduction of lymphoedema in the lower leg.

The fit of the compression hosiery during the course of the treatment will change, as the swelling responds to the treatment and reduces, leading to the hosiery becoming a looser fit. When this happens, the patient is supplied with a new hosiery item of a more appropriate size, which may be smaller or larger, to maintain the applied pressure at the required level. Sub-hosiery pressures will be largely determined by three factors: the material from which the hosiery is manufactured; the size and shape of the limb of the patient; and the activity level of the patient wearing the hosiery. Compression hosiery is characterized by a number of technical standards relating to the compression they apply.

The method of monitoring the physiological changes in a patient of the present invention is particular useful in monitoring the treatment of such swelling and the fitting of the patient with new surgical hosiery. Typically, new compression hosiery is checked one week after being fitted. The patient is generally reviewed and remeasured on a regular basis, for example at 3 to 6 month intervals. In addition, the patient should be remeasured and refitted with hosiery as necessary if there are any significant changes in the size of the limb. Accordingly, the method of the present invention is particularly advantageous in greatly reducing the time taken for each of the very many measuring and fitting sessions a patient must undergo throughout the treatment term. The method of the present invention may be applied in a similar way to the application by a clinician to a patient of compression bandaging. Such compression bandaging is generally provided in hospitals or clinics by specialized orthotic fitters. Compression bandaging is applied to severe cases, where the degree of compression achievable using compression hosiery is not sufficient, for example in the treatment of active ulceration. British Standard BS 6612:1985 provides for three classes of compression stockings, applying compression ranging from 14 to 35 mmHg at the ankle of the patient. When compression above this range is required, compression bandaging is employed. Again, compression bandages are categorized into three types, according to the level of compression capable of being applied.

The method may be employed in a similar manner to provide other support garments, as applied to the provision of compression hosiery.

To provide a proper comparison between the limb of the patient at various times as the treatment progresses, it is preferred that the affected portion of the patient is scanned on each occasion to provide a 360 degree image data set, that is a set of image data that may be used to prepare a 360 degree model of the portion of the patient. This is particularly advantageous when the treatment entails the fitting of a surgical stocking or the like that needs to be fit precisely to the dimensions of the patient's limb.

In a preferred embodiment, the method of the present invention entails identifying a predetermined set of measurement criteria for the affected portion of the patient. After each successive scanning and imaging of the patient, the predetermined measurement criteria are extracted from the 3D image data set and used to provide a comparison for the healthcare specialist. For example, the predetermined set of measurement criteria may be a series of measurements taken from the 360 degree image data set that represent the circumference of the limb at rest at a number of positions along the limb.

In a further embodiment, the method provides a full colour image of the limb of the patient at each fitting, which in addition to determining any change in dimensions of the area undergoing treatment, allows the clinician to carry out a visual comparison, for example to monitor changes in the condition of the skin and the like.

The present invention also provides a system for monitoring the physiological changes in a subject, the system comprising:

an imaging system for scanning a portion of the subject to be monitored to provide a 3D image data set;

a data storage means for storing the 3D image data set;

a processor for comparing a first 3D image data set with a second 3D image data set retrieved from the data storage means;

a display for displaying one or more of the first 3D image data set, the second 3D image data set and the results of the comparison of the first and second 3D image data sets.

A further aspect of the present invention relates to the fitting and manufacture of a surgical support stocking or the like. Accordingly, this aspect of the present invention provides a method of manufacturing a medical support, such as compression hosiery or a support stocking or the like, comprising the steps of:

obtaining a 3D image data set of the portion of the subject requiring support; and employing the 3D image data set or a set of parameters derived from the 3D image data set to prepare a medical support to fit the imaged portion of the subject.

The entire 3D image data set may be employed in the preparation of the medical support. Alternatively, key parameters relating to the size and shape of the imaged portion of the subject may be extracted and these parameters used directly in the manufacture of the support. In particular, the 3D image data set may be reduced to a set of predefined default measurements corresponding to those employed by the manufacturer of the medical support.

As noted above, it is particularly preferred that the 3D image data set comprises a 360 degree data set of the imaged portion. The 360 degree data set may be obtained using an imaging system comprising two cameras and two projectors, with a processor capable of carrying out image interpolation at the interface of the two images. More preferably, the 360 degree image data set is obtained using an array of at least three cameras and projectors.

The method of the present invention may be applied in the manufacture of any medical support device, such as a medical stocking or compression hosiery, for example an anti-embolism stocking. Other support devices that may be prepared using this method include supports for the upper or lower leg, the upper or lower arm, wrist, elbow, neck, stomach and back.

A further application of the general aspects of the present invention is in the preparation of items of clothing in general, in particular any item of clothing that must be tailored or accurately fit to the body of the subject. Specific examples include the preparation of safety garments and items, such as helmets. Accordingly, in still a further aspect, the present invention provides a method for preparing an item of clothing for a subject, the method comprising:

scanning a portion of the subject to be covered by the item to produce a 3D image data set;

generating a three dimensional replica of the portion of the subject from the 3D image data set; and preparing an item of clothing using the three dimensional replica.

As the item of clothing may be prepared at a location remote from the location in which the subject is scanned and the 3D image data set prepared, the invention also provides a method for preparing an item of clothing for a subject, the method comprising:

providing a 3D image data set obtained from scanning the portion of the subject to be covered by the item;

generating a three dimensional replica of the portion of the subject from the 3D image data set; and preparing an item of clothing using the three dimensional replica, Again, the techniques hereinbefore described may be used to obtain the 3D image data set.

The method of this aspect of the invention may be used to prepare any item of clothing that requires fitting to the person in question. Specific examples include helmets, gloves, shoes, boots and the like. The method is particularly suitable for preparing safety items, in particular safety helmets, crash helmets and the like. In addition, the method finds particular application in the production of gas masks, diving masks and masks used for delivering air or oxygen to subjects in oxygen deficient environments, such as at high altitude, in polluted atmospheres and when oxygen enriched air is required.

In addition, the method may be employed to prepare portions of garments or clothing, in particular the portions of items intended to provide impact resistance and protection. Examples include the inserts provided for items of clothing to protect the users arm, elbows, shoulders, thighs, back, legs, knees, etc. from impact and abrasion. The method is also suitable for the preparation of bullet resistant and bullet-proof clothing items.

Accordingly, the term 'clothing' is to be interpreted broadly, in line with the general and specific description set out hereinbefore.

If required, the method may omit the step of preparing a replica using the 3D image data set, which is in turn used in the preparation of the item of clothing. In such a case, the item of clothing is prepared directly from the 3D image data set or from a predetermined set of criteria extracted from the 3D image data set.

Finally, the scanning and imaging techniques of the present invention may be used in the selection and fitting of garments or other items to be worn by a person. Accordingly, in a further aspect, the present invention provides a method for selecting an item of best fit for a person, the method comprising the steps of:

providing a 3D image data set obtained from scanning the portion of the subject to be covered by the item;

relating the image data set to a set of characteristics of items to be selected to identify the characteristics of a best-fit item; and selecting an item on the basis of the best-fit characteristics.

The method may include the step of preparing the 3D image data set, as hereinbefore described.

The method is particularly advantageous in the fitting of a person with items or garments that require an accurate fit to the subject. An example is the fitting of face masks, such as gas masks, that must provide an air-tight seal with the face and head of the subject person. Given the very many variations in the shape and size of the human form, it is often difficult to fit a face mask, gas mask or respirator. If the preparation of a custom, dedicated item to the individual person is not possible, it is necessary to select the item of best fit from a collection of items of varying sizes. This has been carried out on a trial-and-error basis or with the use of only very rudimentary measuring of the subject person.

The method of this aspect of the present invention is also of use in the correct selection and fitting of compression hosiery items, in a manner as described hereinbefore. Patients may be measured and fitted with custom-made compression hosiery during treatment by a clinician at a hospital or clinic. In addition, patients are measured for and purchase compression hosiery items in pharmacies and the like. Further, patients may also be measured for compression hosiery while be treated at home. Such measurements are carried out be a healthcare worker, nurse or pharmacist, who then select the item of the correct size from those held in stock or placed on order. In this respect, compression hosiery is divided into three classes, 1, 2 and 3, depending upon the level of compression to be applied.

The method may be applied in the fitting of other items and garments, where determining the correct size is important. A further example is the fitting of shoes and other footwear for children. The fitting of shoes and footwear for children requires frequent and accurate measurement. Existing methods and systems for measuring the feet of children provide an indication of the length and width dimensions. However, in general, they do not provide any form of indication of the height of the child's foot. An advantage of the method of the present invention is that the imaging steps produce a set of image data that correlate directly to the volume of the imaged subject. Accordingly, the method of the present invention provides an accurate indication of the size of the child's foot in all aspects, not just in two dimensions. Accordingly, the 3D image data set can be used to provide a much more accurate indication of the appropriate shoe or other item to be selected from the stock held. The imaging system of the present invention is compact enough and simple enough to operate that it can be provided in shops and other retails outlets, for general use by customers.

The method of present invention overcomes the difficulties with known fitting practices and allows for a very accurate assessment of the subject person to be obtained, which may then be matched quickly and easily with the best-fit item from the stock of items available. If no suitable item exists, for example no item in stock can provide the minimum required fitting to the person in question, the method can be used to highlight this and generate a warning or alarm.

The present invention also provides a system for selecting an item of best fit for a person, the system comprising:

an imaging system for scanning the subject to be fitted to provide a 3D image data set;

a data storage means for storing a library of records of product details;

a processor for comparing the 3D image data set with records retrieved from the data storage means and identifying the product of best fit;

a display for displaying an identification of the product of best fit.

The system may further comprise an alarm, the alarm being triggered by the processor in the event that a best fit product cannot be located within the records stored in the data storage means.

In one embodiment, the processor is arranged to extract from the 3D image data set a set of predetermined characteristics, the processor comparing the set of predetermined characteristics with the records of product details, in order to make the selection of the best fit product. In this way, products may be characterized by a simple set of characteristics, such as dimensions or volume, making their characterization by manufacturers simpler and the comparison of data to be carried out by the processor more rapid.

Embodiments of the present invention will now be described, by way of example only, having reference to the accompanying drawings, in which.

Figure 1:
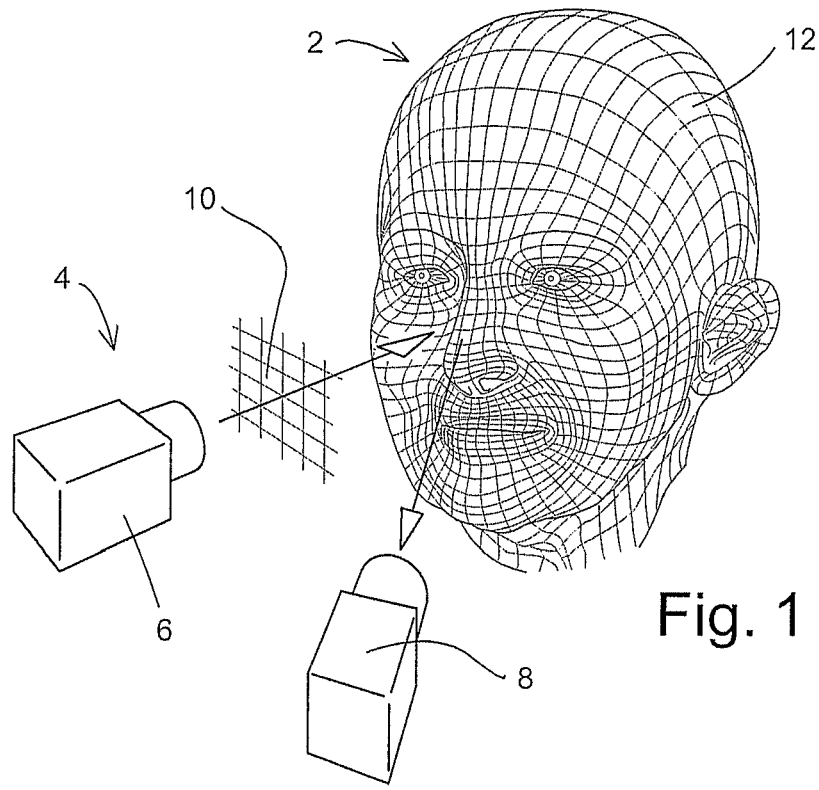
FIG. 1 is a representation of the scanning and imaging of the head of a subject according to a first embodiment of the present invention.

Referring to FIG. 1, there is shown the head of a patient, generally indicated as 2. The system shown in FIG. 1 may be used when the patient is to be fitted with a medical restraint. Similarly, the system of FIG. 1 may be used to fit the subject with a face mask, such as a respirator or gas mask. An imaging system for preparing a 3D image data set of the head 2 of the patient is generally indicated as 4 and comprises a projector 6 and a digital camera 8. The projector 6 projects an array of lines onto the face of the subject, represented by the grid 10. The projected array appears as a set of contour lines 12 on the head 2 of the patient. The camera 8 captures a digital image of the projected lines 12 on the head 2 of the subject. The image of the projected lines 12 is used to prepare a 3D image data set accurately representing the face and head of the subject, for use in the subsequent steps in the method, as described hereinafter.

Figure 2:
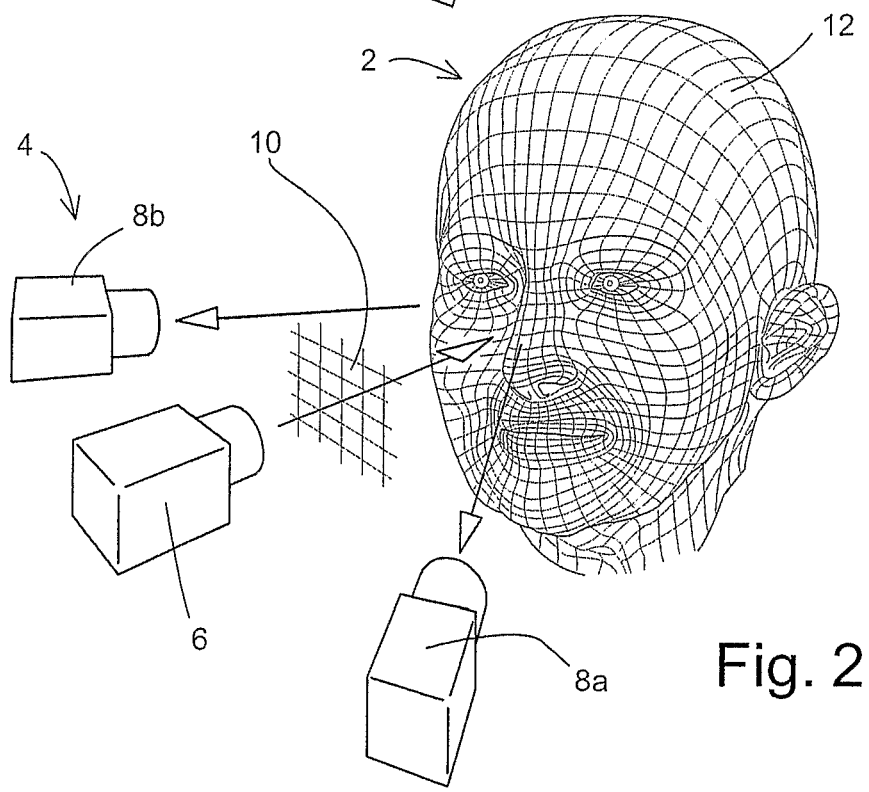
FIG. 2 is a representation of the scanning and imaging of the head of a subject according to a second embodiment of the present invention.

Referring to FIG. 2, there is shown an alternative embodiment of the present invention, in which the imaging system 4 comprises a single projector 6 and a pair of digital cameras 8a and 8b. Each camera 8a and 8b is used to capture a separate image of the projected lines 12 on the head 2 of the subject. The cameras 8a and 8b are disposed on opposite sides of the projector 6, such that each camera will capture a different image of the head 2 of the subject. In this way, portions of the face or head of the subject which may not be captured by a single camera will be present in at least one of the images produced by the cameras 8a and 8b. The two images produced by the cameras 8a and 8b are combined to form a single 3D image data set representing the head 2 of the patient. By having two cameras, 8a and 8b, an improved 3D data set can be obtained, containing more complete information of the shape and configuration of the subject's head 2.

Figure 3:
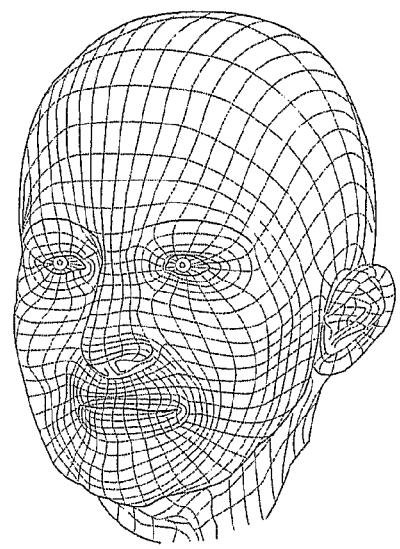
FIG. 3 is a representation of the 3D image data set generated by the scanning and imaging systems of FIGS. 1 and 2.

Referring to FIG. 3, there is shown a representation of the 3D image data set corresponding to the total portion of the head of the subject to be restrained, as generated by the systems of FIGS. 1 and 2. The 3D image data of FIG. 3 may be used in the production of the clinical restraint, as described hereinafter.

Figure 4:
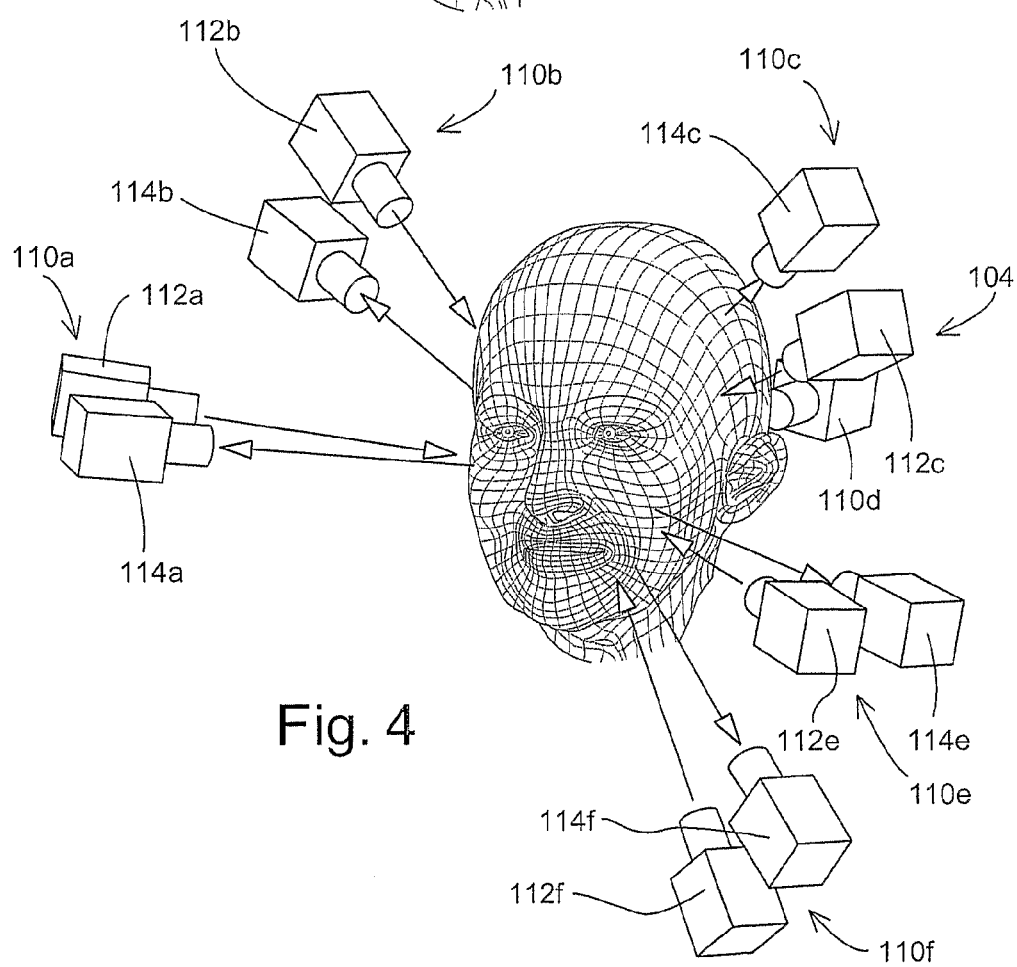
FIG. 4 is a representation of an imaging system according to the present invention for generating a 360 degree image data set.

For many applications falling within the scope of the present invention, it is necessary to generate a 3D image data set that represents a more substantial portion of the subject than possible with the systems of FIGS. 1 and 2. In such a case, the imaging system is provided with a greater number of cameras and, most preferably, a plurality of projectors. In one embodiment, the imaging system comprises a plurality of imaging sub-systems, each sub-system comprising a projector and a camera. Shown in FIG. 4 is an imaging system, generally indicated as 104, for obtaining a 360 degree image of a subject or a portion of a subject, in this case the head of a subject. The imaging system 104 comprises a plurality of imaging sub-systems, indicated as 110a to 110f, each of which has a respective projector 112a to 112f and a respective camera 114a to 114f. As before, each projector 110a to 110f projects an array of lines onto the head of the subject, with each camera capturing an image of the head. As will be noted, the sub-systems 110a to 110f are arranged around the head of the patient, such that when the images of the cameras 114a to 114f are combined, a 360 degree 3D image data set of the head of the subject is obtained. It will be appreciated that fewer imaging sub-systems may be employed in cases where less than 360 degree imaging is required.

Figure 5:
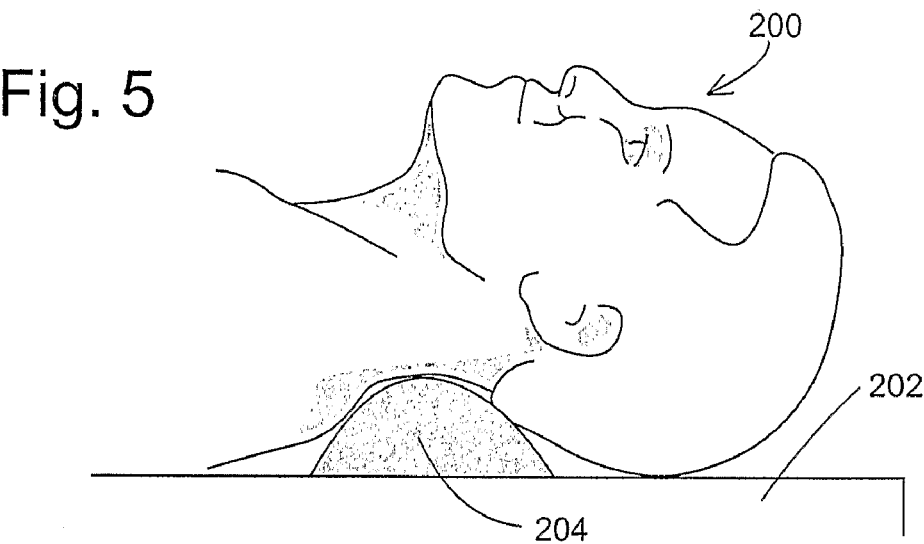
FIG. 5 is a representation of the head and shoulders of a patient to be fitted with a medical restraint.
Figure 6:
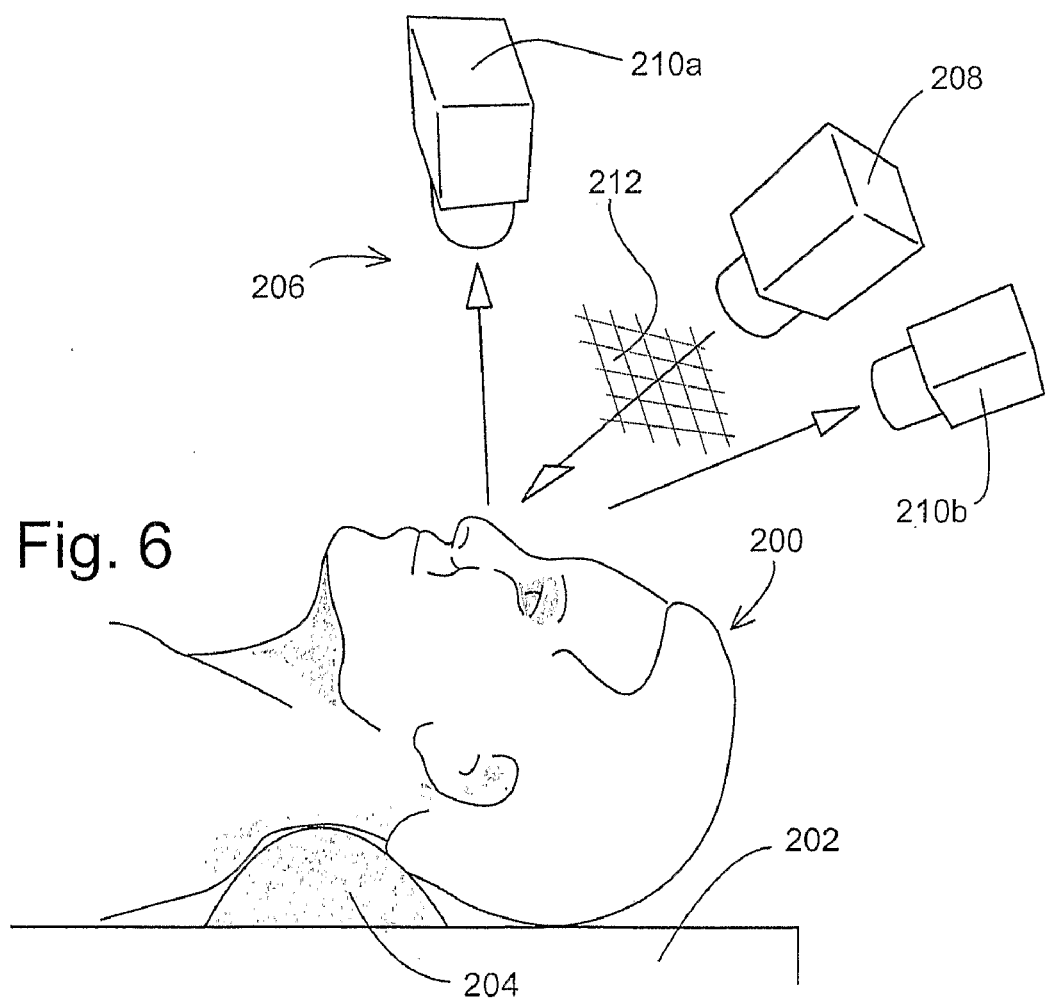
FIG. 6 is a representation of the patient of FIG. 5 being imaged.

When radiotherapy treatment is being applied, the patient is generally lying prone on the treatment table facing upwards. FIG. 5 represents a patient 200 lying on such a treatment table 202. The patient 200 is lying with their neck supported by a neck rest 204. The neck rest is designed and shaped to support the head and shoulders of the patient in the appropriate position for radiotherapy. The angle and orientation of the head of the patient is determined in large part by the shape and height of the neck rest 204. As the patient is to be treated in the position shown in FIG. 5, the medical restraint to immobilize the patient must conform to this position. Accordingly, the head of the patient is imaged while in the treatment position, as represented in FIG. 6. As shown in FIG. 6, an image data set is obtained using an imaging system, generally indicated as 206, having a single projector 208 and two cameras 210a and 210b. As described hereinbefore, the projector 208 projects an array of lines onto the head of the patient, represented by the grid 212.

Figure 7:
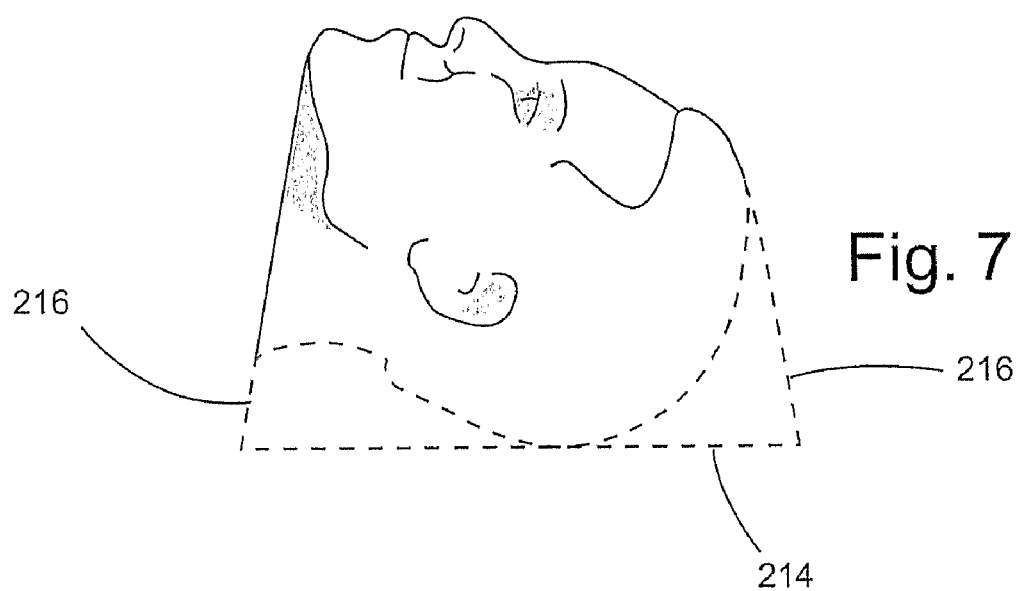
FIG. 7 is a representation of the image data set captured using the system of FIG. 6 undergoing processing and modification.

The image data captured by the cameras 210a and 210b are processed and combined to form a single image data set, represented in FIG. 7. At this stage, the image data set is processed and modified. In particular, the image of the patient captured by the cameras 210a and 210b will contain features that are undercut, such as the patient's ears, neck and the back of the head. The image processing removes the undercuts from the image data set. In addition, the image processing extends the image to a line 214 corresponding to the upper surface of the treatment table. In this way, the final restraint will extend to the treatment table, where it can be secured, to immobilize the patient, as will be described and shown hereinafter. Finally, the image data set is modified as shown in FIG. 7 to have the draft necessary for the restraint to be properly formed. The draft is represented in FIG. 7 by the lines 216 providing the overall image with a generally upwardly tapered form.

Figure 8:
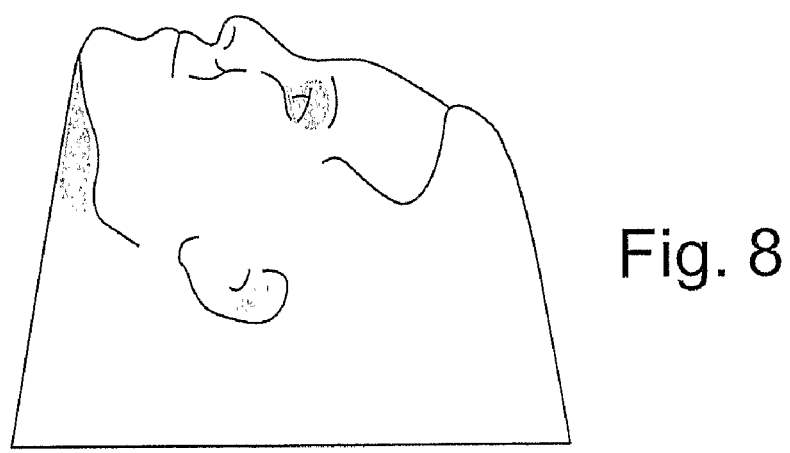
FIG. 8 is a representation of the completed 3D image data set showing a side elevational view of the head of the patient.

A representation of the completed 3D image data set is shown in FIG. 8. The processing of the captured image data to generate the 3D image data set may be accomplished by a suitable processor using appropriate imaging software that form part of the imaging system. Alternatively, the raw image data may be dispatched to a remote processor for the 3D image data set to be prepared.

It will be appreciated that the representation of the image shown in FIGS. 7 and 8 is a side elevation of the head of the patient. However, in practice, the method of the present invention provides a 3D image data set that includes features of all surfaces of the patient's head, such that a 3D replica may be formed.

Figure 9:
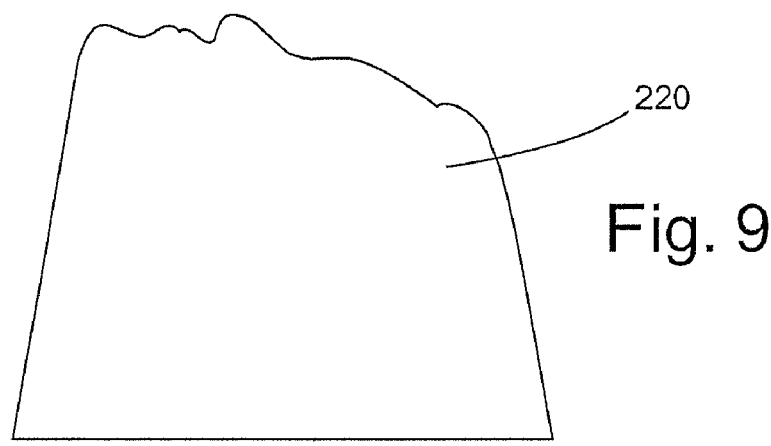
FIG. 9 is a cross-section of the replica corresponding to the 3D image data set of FIG. 8.
Figure 10:
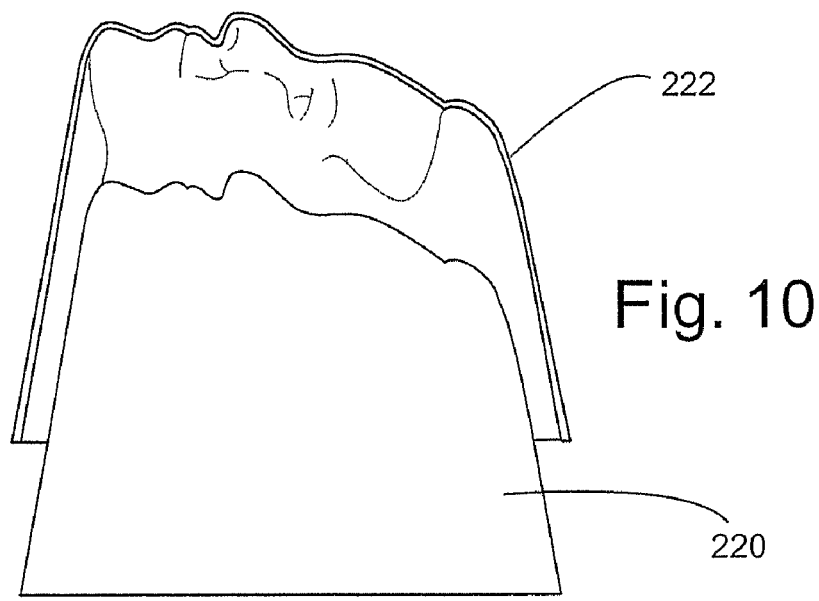
FIG. 10 is a cross-sectional representation of the formation of a medical restraint using the replica of FIG. 9.
Figure 11:
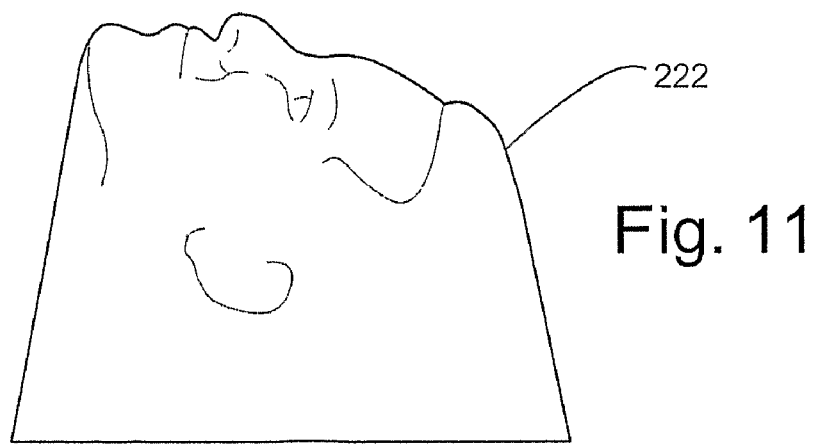
FIG. 11 is a representation of the side elevation of the raw restraint formed as shown in FIG. 10.

Once the 3D image data set is complete, a replica of the head of the patient is prepared using the 3D image data set. The replica corresponding to the 3D image data set of FIG. 8 is shown in cross-section in FIG. 9. The replica is used to form the medical restraint. This step is represented in FIG. 10, in which the replica 220 is shown in cross-section, with a vacuum-formed raw restraint 222, also shown in cross-section is being removed. The draft applied during the processing of the raw image data to prepare the 3D image data set is necessary to allow the raw restraint 222 to be easily released from the replica 220, as shown in FIG. 10. The raw restraint 222 is shown in side elevation in FIG. 11.

Once the raw restraint has been prepared, it is finished, in particular by being cut to size to remove the excess material. In addition, holes are cut in the restraint corresponding to the eyes, nose and mouth of the patient. A completed restraint 230 is shown in side elevation in FIG. 12. As noted above, these features may be formed according to a set of standard procedures. Alternatively, they may be based upon data input by the clinician having reviewed the image data when prepared.

Figure 12:
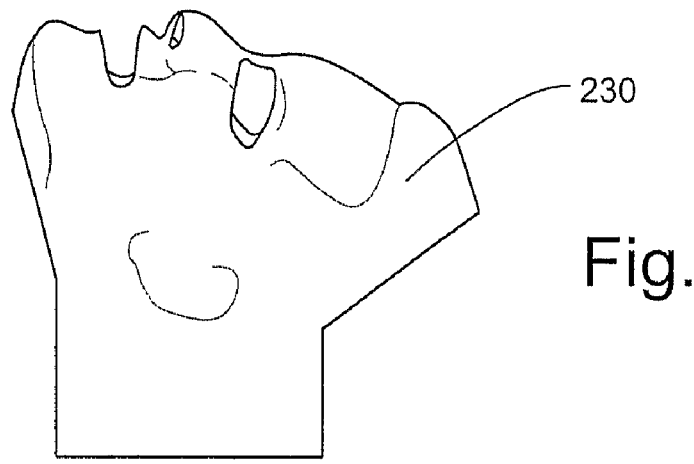
FIG. 12 is a representation of the side elevation of a completed restraint corresponding to the raw restraint of FIG. 11.
Figure 13:
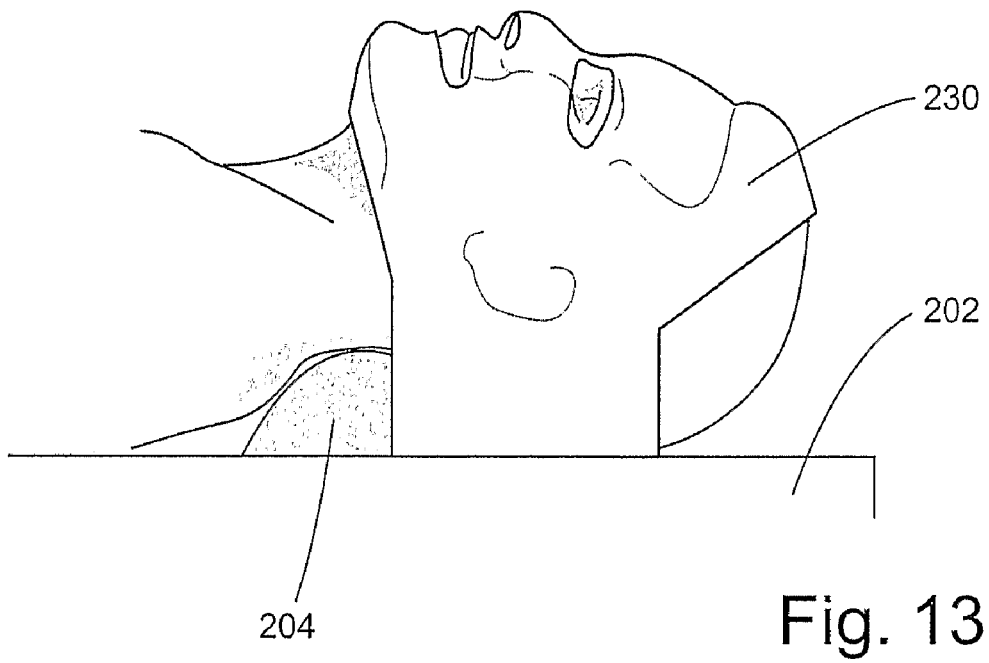
FIG. 13 is a side elevation of the restraint of FIG. 12 in position on a patient lying on a treatment table.

Referring to FIG. 13, the restraint 230 of FIG. 12 is shown in position on the head of the patient. As will be noted, the patient is lying on the treatment table 202, with the neck rest 204 in place. The restraint 230 extends at the sides to the treatment table, where it is secured by suitable means, such as clamps or the like (not shown for clarity).

Figure 14:
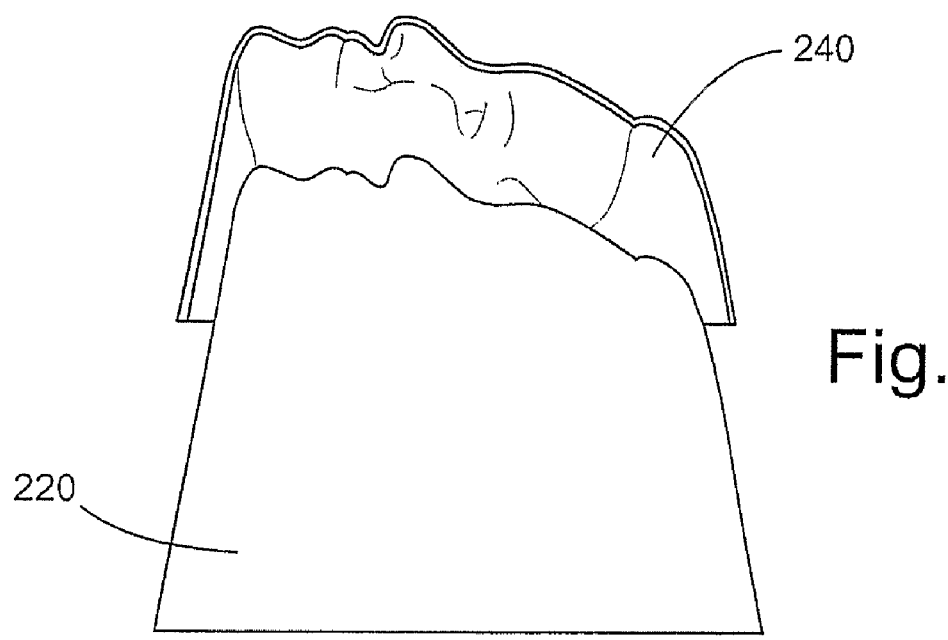
FIG. 14 is a side elevation of an underlay according to a further embodiment of the present invention being prepared using the replica of FIG. 9.
Figure 15:
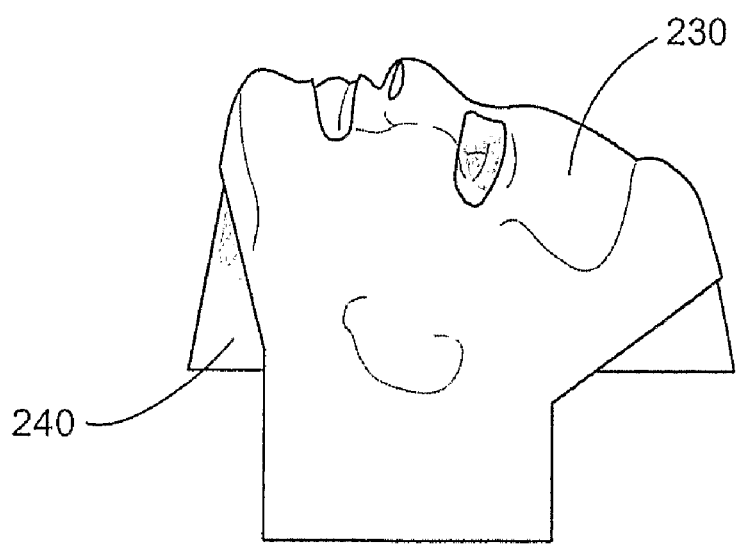
FIG. 15 is a further view of the restraint of FIG. 12 in combination with the underlay of FIG. 14.

In one embodiment of the present invention, an underlay bearing a full colour image of the relevant portion of the patient is prepared using the replica. Thus, there is shown in FIG. 14, an underlay 240 being vacuum formed on the replica 220 shown in FIG. 9. The underlay 240 is prepared from a sheet of plastic material onto which has been printed a colour image texture of the face of the patient. The sheet is then vacuum formed on the replica 220 to form a three-dimensional underlay. FIG. 15 shows the underlay 240 in combination with the restraint 230 of FIG. 12. The features of the colour image on the underlay 240 are visible through the restraint 220, allowing the clinician to prepare for the treatment in advance of the patient arriving.

Figure 16:
FIG. 16 is a further view of an alternative embodiment of the present invention in which the replica of FIG. 9 is provided with a coloured image on its surface.
Figure 17:
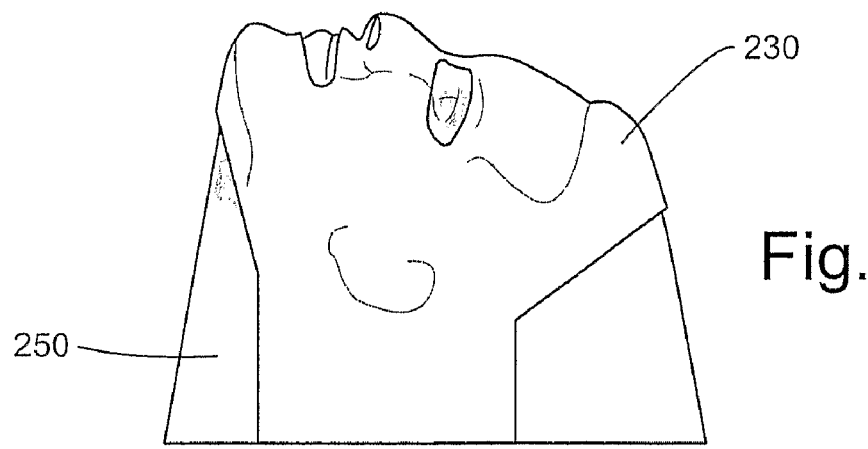
FIG. 17 is a side elevational view of the coloured replica of FIG. 16 with the restraint of FIG. 12 in place.

In an alternative embodiment, the replica may be formed with a full colour image of the relevant portion of the patient on its surface. Thus, the replica 220 shown in FIGS. 9 and 10 may be formed with a full colour image of the face of the patient, In this way, the clinician is provided with the restraint, together with an accurate image of the patient to be treated, allowing the clinician to prepare for the treatment session in advance of the patient's arrival. This minimizes the length of time the patient is required to remain immobilized by the restraint. Thus there is shown in FIG. 16 a restraint 230 (represented in cross-section) being applied over a full colour replica 250. The surface of the replica 250 has been prepared with a colour image of the face of the patient. The full colour image is provided as a part of the 3D image data set produced during the imaging and image processing stage. The restraint 230 is shown in position on the coloured replica 250 in FIG. 17, which indicates how the clinician may use the replica and restraint to review the patient's treatment without the need to have the patient present and immobilized by the restraint.

Figure 18:
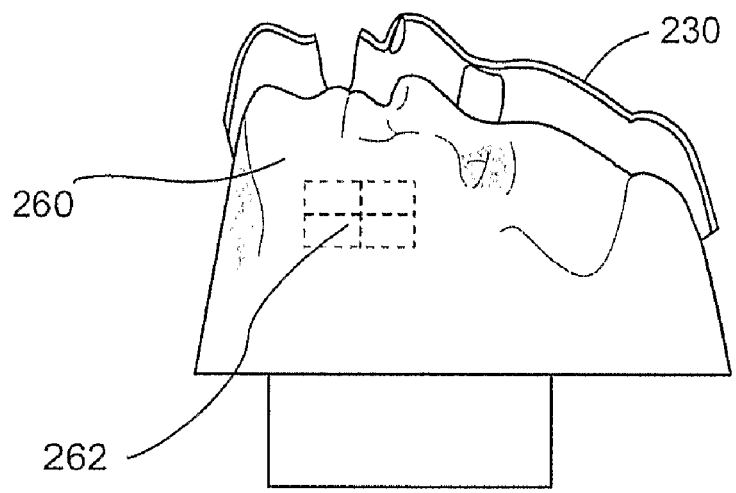
FIG. 18 is a side view of the underlay of FIG. 14 bearing treatment marks in combination with the restraint of FIG. 12.
Figure 19:
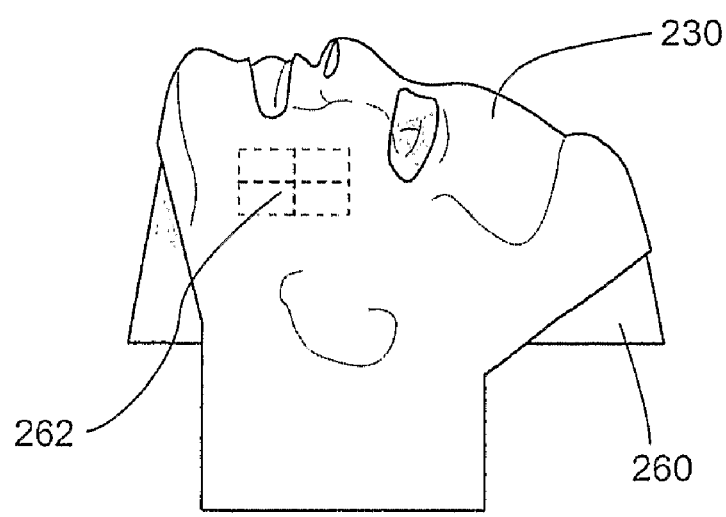
FIG. 19 is a side elevational view of the underlay of FIG. 18 and the restraint.

During the course of radiotherapy, the clinician will often need to rely upon marks and indications to irradiate the patient accurately. These can be applied to the skin of the patient. However, they are more preferably incorporated into the restraint or the underlay of the present invention. Accordingly, the treatment marks may comprise part of the 3D image data set provided by the clinician as a result of the scanning steps of the present invention. Referring to FIG. 18, there is shown a restraint 230 (in cross-section) overlying an underlay 260. The underlay bears a set of treatment marks 262 prepared to guide the clinician during the treatment of the patient. As shown in FIG. 19, the treatment marks 262 on the underlay 260 are visible through the restraint 230.

The underlay bearing the full colour image of the subject is of particular use in the finishing of the restraint or mask, as hereinbefore described. In particular, the use of the underlay allows the holes for the patient's eyes, nose and mouth to be accurately positioned and sized, leading to an accurate restraint that is both comfortable and practical for the patient to wear, while also immobilising the patient as required.

Figure 20:
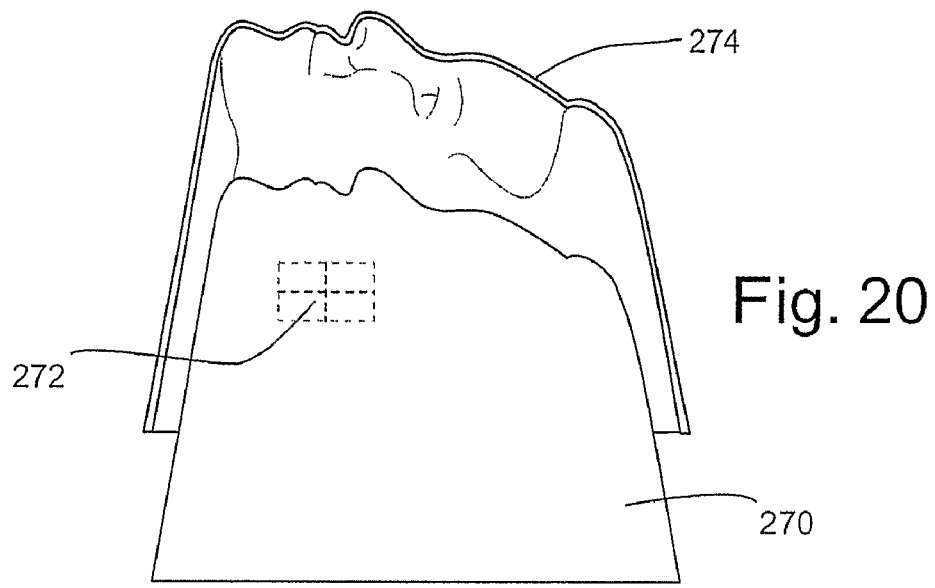
FIG. 20 is a side elevational view of a restraint being formed on a replica of according to a further embodiment of the present invention.
Figure 21:
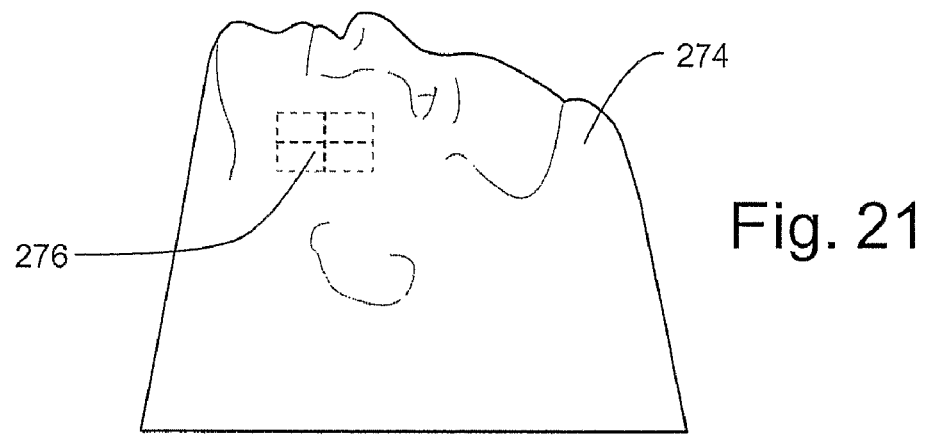
FIG. 21 is a side elevational view of the raw restraint prepared as shown in FIG. 20.
Figure 22:
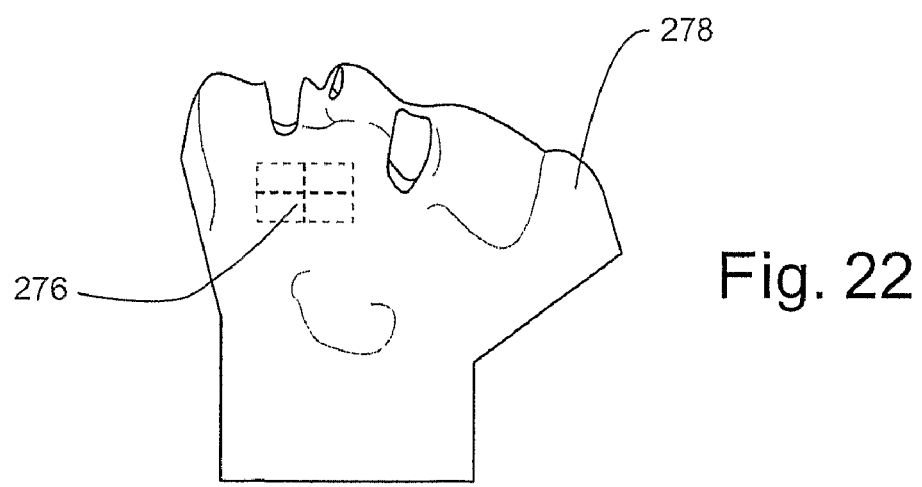
FIG. 22 is a side elevational view of the completed restraint corresponding to the raw restraint of FIG. 21.

In a further arrangement, which may be used either as an alternative to or in conjunction with the features of the embodiments of FIGS. 18 and 19, the treatment marks are provided as part of the 3D image data set so as to appear on the surface of the replica. Thus, referring to FIG. 20, there is shown a replica 270 bearing a set of treatment marks 272 to provide an indication for the clinician during the treatment of the patient. The treatment marks have been incorporated into the replica following the data provided in the 3D image data set. The treatment marks 272 appear as a set of raised relief marks on the surface of the replica 270. As shown in FIG. 20, a raw restraint 274 is being prepared using the replica 270, by the techniques described hereinbefore, such as vacuum forming. The raw restraint 274 prepared in this way is represented in FIG. 21 and bears on its inner surface a set of treatment marks 276 present in the form of an impression relief. The completed restraint 278 is shown in FIG. 22 bearing the set of treatment marks 276.

Figure 23:
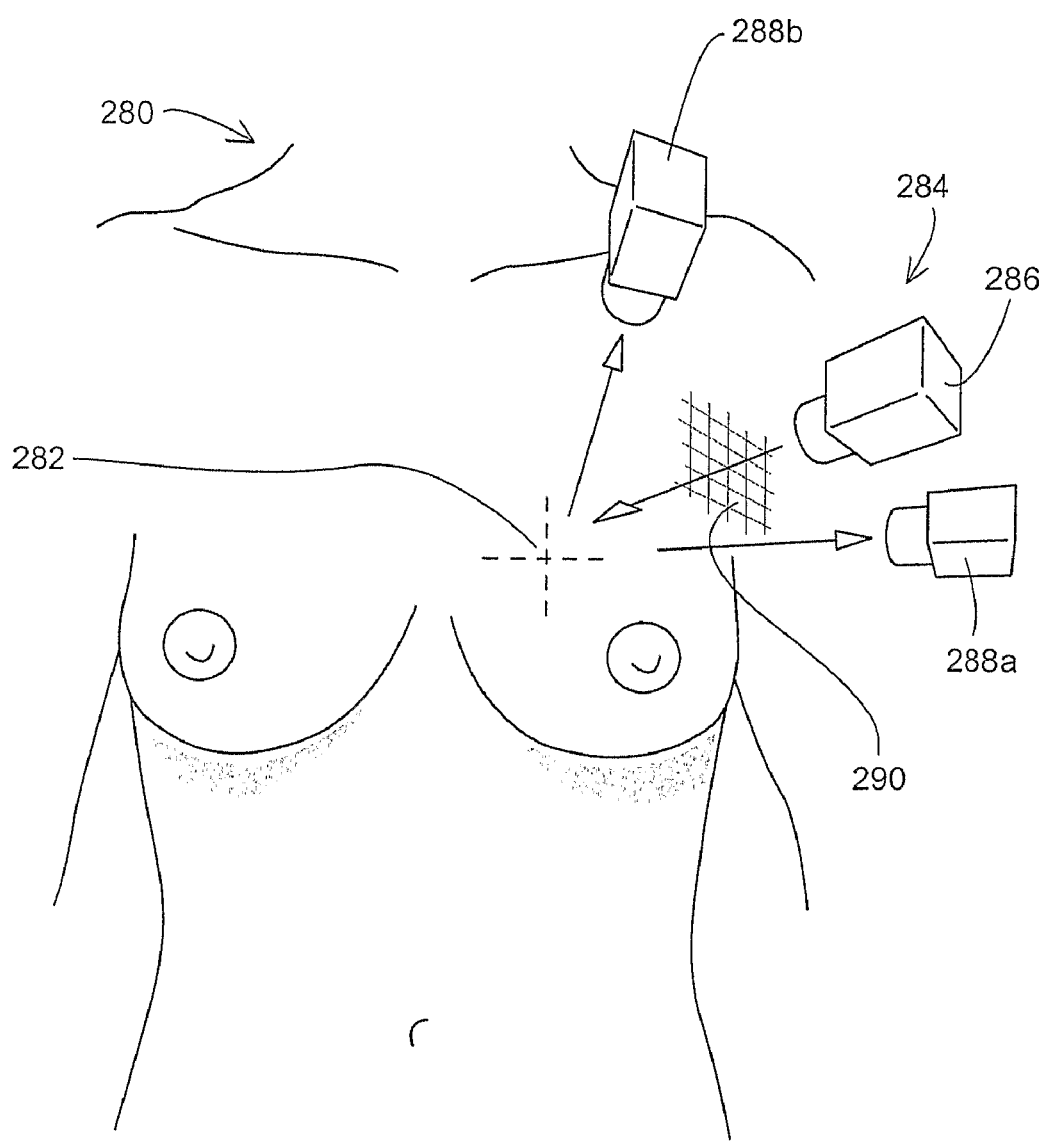
FIG. 23 is a representation of the method of capturing treatment marks in the 3D image data set.

As noted above, the treatment marks provided on either the underlay or the replica and restraint form part of the 3D image data set produced as a result of the imaging and processing stages of the method of the present invention. The capture of the treatment marks is represented in FIG. 23, where a woman, generally indicated as 280, has been marked with a set of treatment marks 282 prior to treatment for breast cancer. An imaging system, generally indicated as 284, comprises a single projector 286 and a pair of digital cameras 288a and 288b. The projector 286 projects an array of lines onto the breast of the patient, represented by the grid 290. Images of the array as projected onto the breast of the patient are captured by both the cameras 288a and 288b, together with the set of treatment marks 282. The treatment marks 282 are thus incorporated into the raw image data set and are retained in the 3D image data set, from which the replica and underlay, if used, are prepared as described hereinbefore.

Figure 24:
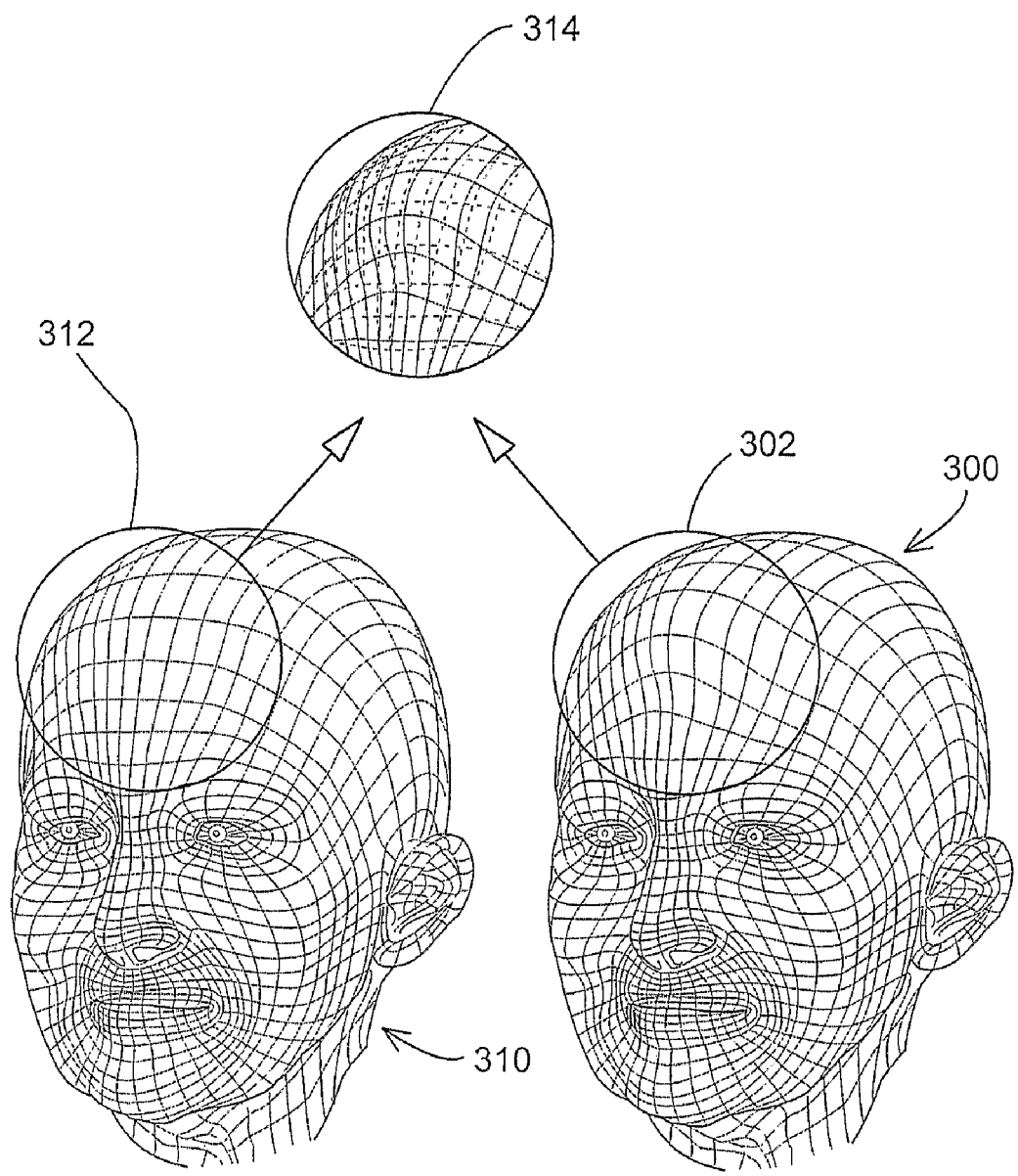
FIG. 24 is a representation of the method of the present invention for monitoring a course of treatment of a patient.

Referring to FIG. 24, there is shown a representation of the method of the present invention applied to monitoring the course of treatment of a patient. In FIG. 24, there is shown a representation of the 3D image data set 300 obtained during an early stage in the treatment of a patient with a tumour in the frontal portion of the head. The 3D image data set 300 has been obtained as a 360 degree image data set using an imaging system of the type shown in FIG. 4 and as described hereinbefore. The portion of the patient of interest is that lying within the circle 302 shown in FIG. 24 positioned approximately at the forehead of the patient. As can be seen in the 3D data set 300, at the time the patient was imaged, the tumour was evidenced by virtue of a considerable swelling of the forehead of the patient. Following a term of treatment of the tumour, a second 3D image data set 310 was obtained in the same manner as before. The region of interest in the second 3D image data set is indicated by the circle 312 in FIG. 24. The method of the present invention comprises comparing the first and second 3D image data sets to determine any change in the shape and/or dimensions of the head of the patient. As represented in the circle 314 in FIG. 24, a comparison of the two image data sets shows that the treatment has successfully reduced the size of the tumour, as evidenced by the reduction in swelling and change in shape of the forehead of the patient.

Figure 25:
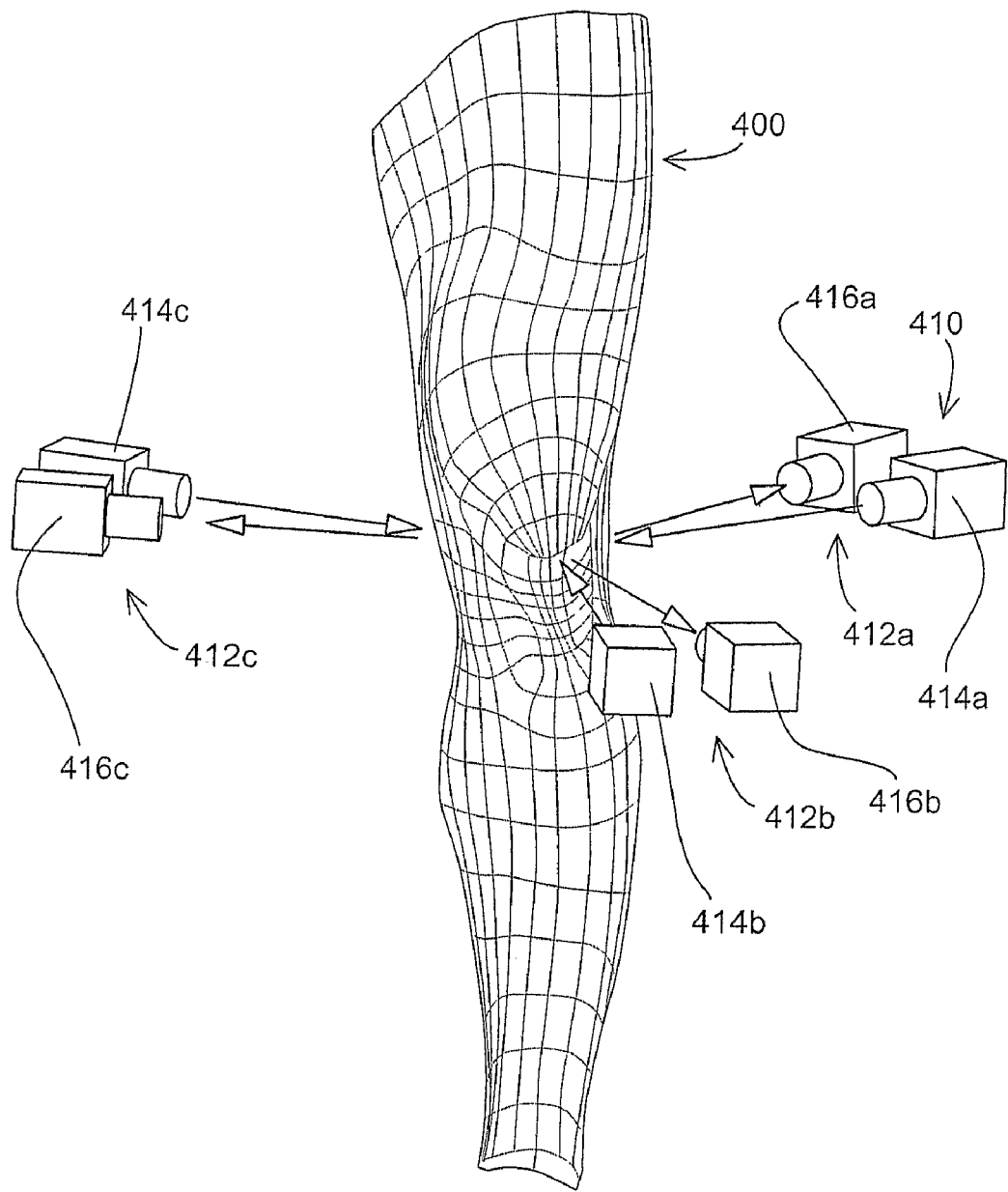
FIG. 25 is a representation of the method of imaging the leg of a patient for the fitting of a compression hosiery.

As discussed hereinbefore, the imaging and image processing method of the present invention may be applied in the fitting of items and garments to a subject, in particular the fitting of medical compression hosiery to a patient. This method is represented in FIG. 25 where there is shown the leg of a patient undergoing imaging. The leg of the patient, generally indicated as 400, is imaged using an imaging system generally indicated as 410 and comprising three imaging sub-systems 412a, 412b and 412c in order to provide a 360 degree image data set. Each imaging sub-system comprises a projector 414a, 414b and 414c and a digital imaging camera 416a, 416b and 416c. The region of the leg 400 above and below the knee of the patient is being imaged to provide a 3D image data set of the region to be treated.

Figure 26:
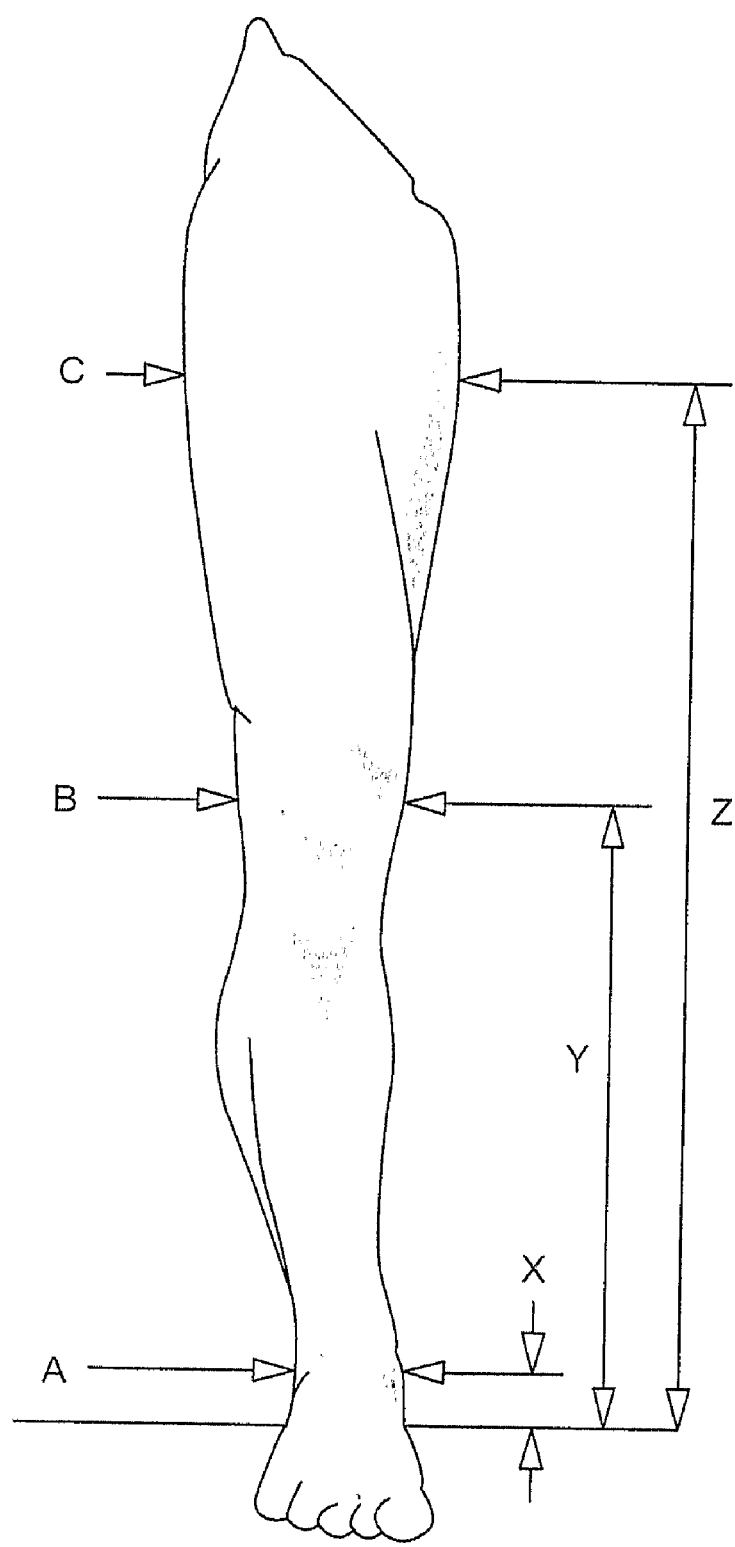
FIG. 26 is a representation of a set of predetermined measurement criteria that may be obtained from the 3D image data set obtained as shown in FIG. 25.

The 3D image data set produced by the method and system represented by FIG. 25 may be used in the manufacture of custom fit compression hosiery. Alternatively, the data set may be used in the selection of a compression hosiery to provide the required range of compression to treat the affected area. In addition, the 3D image data set may be compared with similar image data sets obtained at earlier stages in the treatment of the patient, in order to track and monitor the progress of the treatment. If the 3D image data set is to be used in the manufacture of a custom-fit compression hosiery or in the selection of the appropriate pre-existing hosiery item, the 3D image data may be reduced to a set of predetermined measurement criteria. Thus, there is shown in FIG. 26 a representation of a set of measurements to be derived from the 3D image data set and required to prepared or select the appropriate compression hosiery. The predetermined set of measurements comprise the girth A of the ankle of the patient at a distance X from the ground, the girth B of the knee of the patient at a distance Y from the ground, and the girth C of the thigh of the patient at a distance Z from the ground. Such a set of measurements may be used in the manufacture or fitting of compression hosiery. In addition, a database may be constructed of such measurements in order to track the progress of the treatment of the patient.

The invention claimed is:

1. A method for preparing a clinical restraint for a subject, the method comprising:
   providing a 3D image data set obtained from scanning the portion of the subject to be restrained;
   increasing a size of a portion of the 3D image data set to provide a clearance between the subject and a clinical restraint;
   generating a three dimensional replica of the portion of the subject from the 3D image data set; and
   preparing the clinical restraint using the three dimensional replica.

2. The method of claim 1, wherein the 3D image data set is prepared by a method comprising the steps of:
   illuminating the portion of the subject with a light pattern having a plurality of light planes, the light pattern varying in wavelength spatially across the portion of the subject and wherein said at least one light plane corresponds to at least one angle at which light of that wavelength is emitted and contains only a single spectral component;
   acquiring an image of the portion of the subject thus illuminated using a camera; and
   calculating a distance to a point on said object or in said scene using triangulation based on a baseline distance between said light source and the camera, an angle between the camera and the baseline and an angle at which light striking the point is emitted by the light source as determined from red/green/blue values corresponding to the wavelength of the light striking the point.

3. The method of claim 1, wherein the 3D image data set is prepared by a method comprising the steps of:
   projecting a predetermined pattern of components onto the portion of the subject, the components having a known relative positioning;
   acquiring an image of the portion of the subject; and
   calculating the three-dimensional shape on the basis of relative distances between pattern components as observed in the acquired image.

4. The method of claim 3, wherein absolute dimensions of the shape or image are obtained by fixing an appropriate scale factor.

5. The method according to claim 3, wherein relative spatial positions of points on the portion of the subject are calculated directly from relative, observed positions of the components of the image.

6. The method of claim 1, wherein the step of scanning captures a plurality of different raw images of a whole or a part of the portion of the subject, which raw images are combined to form the 3D image data set.

7. The method of claim 1, wherein the 3D image data set is modified prior to being employed in the preparation of the replica.

8. The method of claim 7, wherein the 3D image data set is modified by one or more steps selected from the group consisting of:
- interpolating to fill in missing image data;
- removing undercut portions of the image data;
- providing the image with an appropriate taper or draft for moulding;
- extending the image to provide a region of attachment to a treatment platform or the like; and
- providing one or more holes in the image.

9. The method of claim 1, wherein the replica is provided with indications on its surface for use in guiding the clinical procedure.

10. The method of claim 9, wherein the indications formed on the replica are derived from indications placed onto the surface of the portion of the subject and captured in the image during the imaging step.

11. The method of claim 9, wherein the indications are formed as raised portions of the surface of the replica, such that corresponding impressions are formed on the inner surface of the clinical restraint directly during the step of forming the replica.

12. The method of claim 1, wherein the replica is provided with a full colour image of the portion of the subject on its surface.

13. The method of claim 1, further comprising the step of preparing a flexible layer from the replica.

14. The method of claim 13, wherein the flexible layer is formed as an image on a flat sheet from the 3D image data, the flat sheet being formed around the surface of the replica by means of a vacuum.

15. The method of claim 1, wherein the replica is prepared by a method selected from the group consisting of 3D printing techniques, stereolithography (SLA), vacuum casting, selective laser sintering (SLS), rapid cast metals, direct metal laser sintering (DMLS), laminated object manufacture (LOM), fused deposition modeling, 3D thermojet wax modeler rapid tooling, injection moulding, CNC machining, micro-modeling and blow moulding.

16. The method of claim 1, wherein the replica is prepared in the form of an array of longitudinal movable pins, the displacement of each pin from a datum being determined from the 3D image data, such that the surface of the replica is formed from the ends of the plurality of pins.

17. The method of claim 1, wherein the restraint is transparent in the region of the portion of the subject that requires clinical attention.

18. A system for preparing a 3D image data set for the preparation of a clinical restraint, the system comprising:
- a projector for projecting an array of components onto the surface of the subject to be restrained;
- a camera for capturing an image of the surface to provide raw image data;
- a processor for preparing a 3D image data set from the raw image data;
- a display means for displaying the 3D image data as an image; and
- a processor for modifying the 3D image data set according to one or more predetermined functions that increase a size of a portion of the 3D image data set to provide a clearance between the subject and the restraint, thereby rendering the 3D image data set suitable for use in the preparation of the restraint.

19. The system of claim 18, comprising a plurality of imaging sub-systems, each sub-system comprising a projector and a camera.

20. The system of claim 18, wherein the processor is adapted to combine a plurality of raw images to form the 3D image data set.

21. The system of claim 18, wherein the processor is further adapted to modify the 3D image data set according to a set of predetermined functions that further render the 3D image data set suitable for use in the preparation of the restraint.

22. The system of claim 21, wherein the processor is adapted to modify the 3D image data set by one or more methods selected from the group consisting of:
- interpolating to fill in missing image data;
- removing undercut portions of the image data;
- providing the image with an appropriate taper or draft for moulding;
- extending the image to provide a region of attachment to a treatment platform or the like; and
- providing one or more holes in the image.

23. The system of claim 21, further comprising an interface, whereby an operator may input data for inclusion in the 3D image data set and/or modify the image of the 3D image data set.

\* \* \* \* \*